(12) United States Patent
Hill et al.

(10) Patent No.: US 11,911,767 B2
(45) Date of Patent: Feb. 27, 2024

(54) POSITIVE DISPLACEMENT PIPETTE SYRINGE IDENTIFICATION SYSTEM

(71) Applicant: Mettler-Toledo Rainin, LLC, Oakland, CA (US)

(72) Inventors: Richard Hill, Berkeley, CA (US);
Michael McNaul, Sunnyvale, CA (US);
Bob Wells, Severna Park, MD (US);
Simon Shakespeare, Royston (GB);
Matthew Newman, Oakington (GB)

(73) Assignee: Mettler-Toledo Rainin, LLC, Oakland, CA (US)

( * ) Notice: Subject to any disclaimer, the term of this patent is extended or adjusted under 35 U.S.C. 154(b) by 0 days.

(21) Appl. No.: 16/664,769

(22) Filed: Oct. 25, 2019

(65) Prior Publication Data

US 2021/0121885 A1 Apr. 29, 2021

(51) Int. Cl.
*B01L 3/00* (2006.01)
*B01L 3/02* (2006.01)

(52) U.S. Cl.
CPC ............ *B01L 3/54* (2013.01); *B01L 3/0237* (2013.01); *B01L 3/0279* (2013.01); *A61M 2205/6081* (2013.01)

(58) Field of Classification Search
None
See application file for complete search history.

(56) References Cited

U.S. PATENT DOCUMENTS

| | | | |
|---|---|---|---|
| 4,978,335 A | 12/1990 | Arthur, III | |
| 5,620,661 A | 4/1997 | Schürbrock | |
| 5,770,160 A | 6/1998 | Smith et al. | |
| 6,652,489 B2 | 11/2003 | Trocki et al. | |
| 6,740,295 B2 | 5/2004 | Braun et al. | |
| 6,977,062 B2 | 12/2005 | Cronenberg | |
| 7,731,908 B2 | 6/2010 | Lenz | |
| 8,114,361 B2 | 2/2012 | Reichmuth | |
| 8,114,362 B2 | 2/2012 | Cronenberg | |

(Continued)

FOREIGN PATENT DOCUMENTS

| | | | | |
|---|---|---|---|---|
| CH | 714994 A2 | * | 11/2019 | ........ A61M 5/31545 |
| CN | 102580197 A | | 7/2012 | |

(Continued)

OTHER PUBLICATIONS

Machine-generated English translation of EP 691158 (1996) (Year: 1996).*

(Continued)

*Primary Examiner* — P. Kathryn Wright
(74) *Attorney, Agent, or Firm* — Standley Law Group LLP; Jeffrey S. Standley; Adam J. Smith

(57) ABSTRACT

Described are exemplary embodiments of a syringe identification system for use with a positive displacement pipette, such as a handheld powered positive displacement pipette. An exemplary syringe identification system may include a sensor, such as a color sensor, that is located at or near a distal end of the pipette and arranged such that the sensor is operative to read an identifying marking(s) on a syringe that has been installed to the pipette. The sensor may be a color sensor having an illumination source and configured to read a color code on the syringe. The color code may be usable to identify the syringe to the pipette.

11 Claims, 31 Drawing Sheets

(56) References Cited

U.S. PATENT DOCUMENTS

| | | |
|---|---|---|
| 8,117,928 B2 | 2/2012 | Suovaniemi et al. |
| 8,277,758 B2 | 10/2012 | Mattioli |
| 8,377,396 B2 | 2/2013 | Meinicke et al. |
| 8,632,738 B2 | 1/2014 | Giribona et al. |
| 8,652,418 B2 | 2/2014 | Rempt et al. |
| 8,661,920 B2 | 3/2014 | Molitor et al. |
| 8,813,584 B2 | 8/2014 | Blumentritt et al. |
| 8,839,685 B2 | 9/2014 | Löhn |
| 9,289,762 B2 | 3/2016 | Belgardt et al. |
| 9,403,163 B2 | 8/2016 | Andres et al. |
| 9,579,644 B2 | 2/2017 | Belgardt et al. |
| 10,870,107 B2 | 12/2020 | Setzer et al. |
| 2001/0047153 A1* | 11/2001 | Trocki .............. A61M 5/14546 604/207 |
| 2002/0088131 A1 | 7/2002 | Baxa et al. |
| 2007/0253832 A1 | 11/2007 | Kenney |
| 2010/0164727 A1 | 7/2010 | Bazargan et al. |
| 2011/0018525 A1 | 1/2011 | MacLean et al. |
| 2012/0291567 A1 | 11/2012 | Homberg et al. |
| 2013/0095508 A1 | 4/2013 | Campitelli et al. |
| 2013/0197445 A1* | 8/2013 | Schabbach ........... A61B 5/4839 604/189 |
| 2014/0010732 A1 | 1/2014 | Belgardt et al. |
| 2014/0051182 A1 | 2/2014 | Reichmuth et al. |
| 2014/0260697 A1 | 9/2014 | Staton et al. |
| 2014/0318279 A1 | 10/2014 | Blumentritt et al. |
| 2016/0158742 A1 | 6/2016 | Belgardt et al. |
| 2016/0287815 A1 | 10/2016 | Aoki et al. |
| 2017/0056603 A1* | 3/2017 | Cowan ................ A61M 5/1456 |
| 2017/0151556 A1 | 6/2017 | Wilth et al. |
| 2020/0171481 A1 | 6/2020 | Schraut et al. |

FOREIGN PATENT DOCUMENTS

| | | |
|---|---|---|
| CN | 104027875 A | 9/2014 |
| CN | 104769438 A | 7/2015 |
| CN | 204448046 U | 7/2015 |
| CN | 108201903 A | 6/2018 |
| DE | 102012016020 A1 | 2/2014 |
| DE | 202009019205 U1 | 5/2019 |
| EP | 0155087 A2 | 9/1985 |
| EP | 0584531 A2 | 3/1994 |
| EP | 0657216 A2 | 6/1995 |
| EP | 0691158 A2 | 1/1996 |
| EP | 0776247 A1 | 6/1997 |
| EP | 1344565 A1 | 9/2003 |
| EP | 1724020 A1 | 11/2006 |
| EP | 1825915 A2 | 8/2007 |
| EP | 2033712 A1 | 3/2009 |
| EP | 1724020 B1 | 3/2010 |
| EP | 2574402 B1 | 3/2015 |
| EP | 3434373 A1 | 1/2019 |
| IN | 108136119 A | 6/2018 |
| JP | 2006-231326 A | 9/2006 |
| JP | 2009-500599 A | 1/2009 |
| JP | 4893073 B2 | 1/2012 |
| JP | 2015-221405 A | 12/2015 |
| WO | 2015/179783 A1 | 11/2015 |
| WO | 2016/081595 A1 | 5/2016 |
| WO | 2016/087046 A1 | 6/2016 |

OTHER PUBLICATIONS

Eppendorf AG, Multipette E3/E3x, accessed online at https://online-shop.eppendorf.com/OC-en/Manual-Liquid-Handling-44563/Pipettes-44564/MultipetteE3-E3x-PF-135444.html, 2019, 8 pages.

Eppendorf, Catalog 2018, Liquid Handling, Sample Handling, Cell Handling, 2018, 207 pages, Eppendorf AG, available online at https://www.eppendorf.com/uploads/media/2018_Eppendorf_INT_Catalog_oPoIVD.compressed.pdf.

* cited by examiner

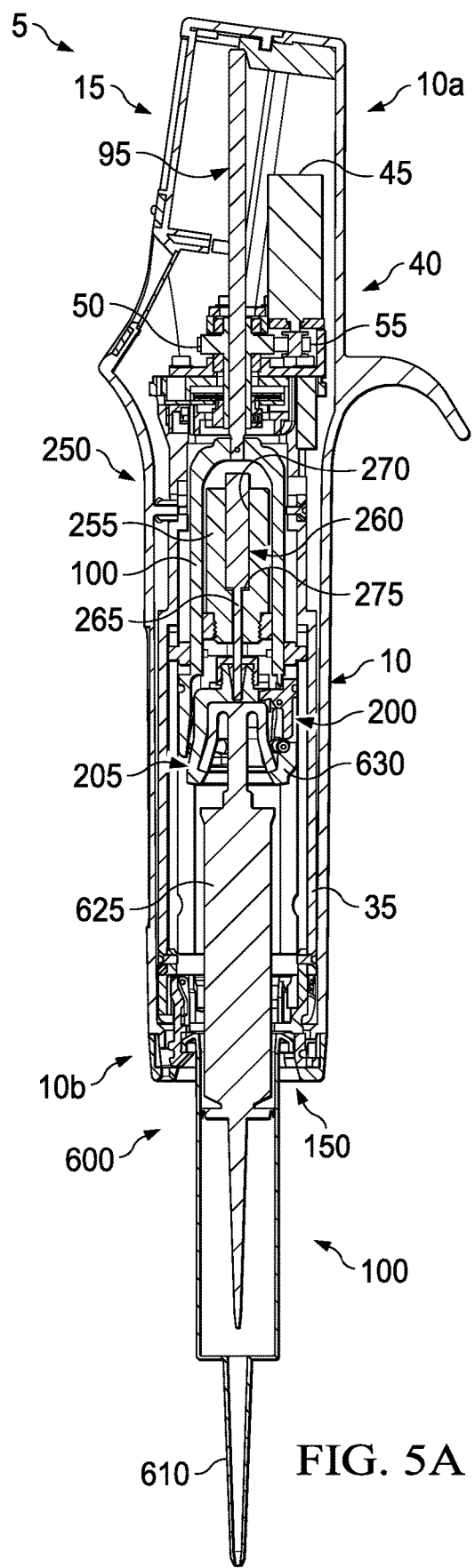
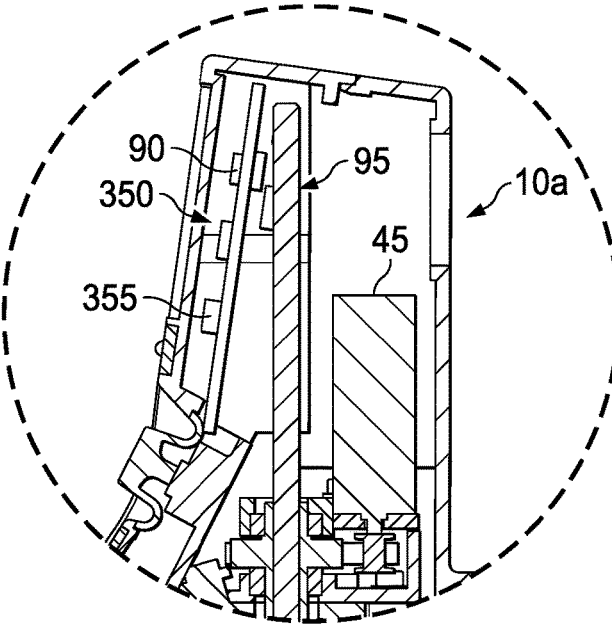
FIG. 5A
FIG. 5B

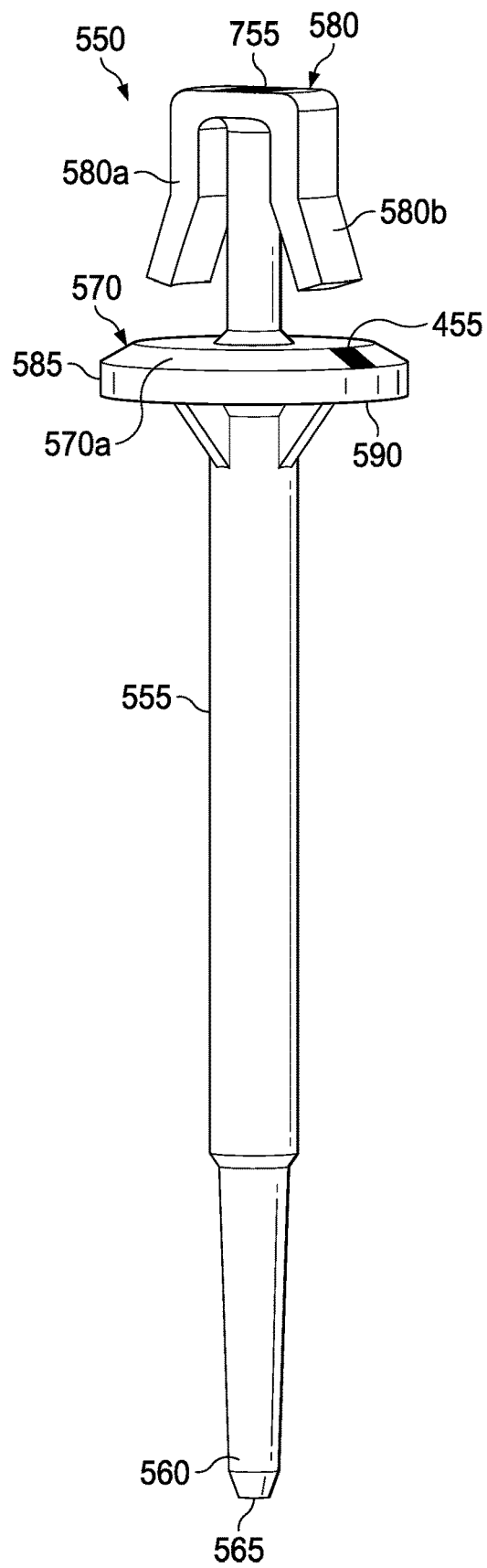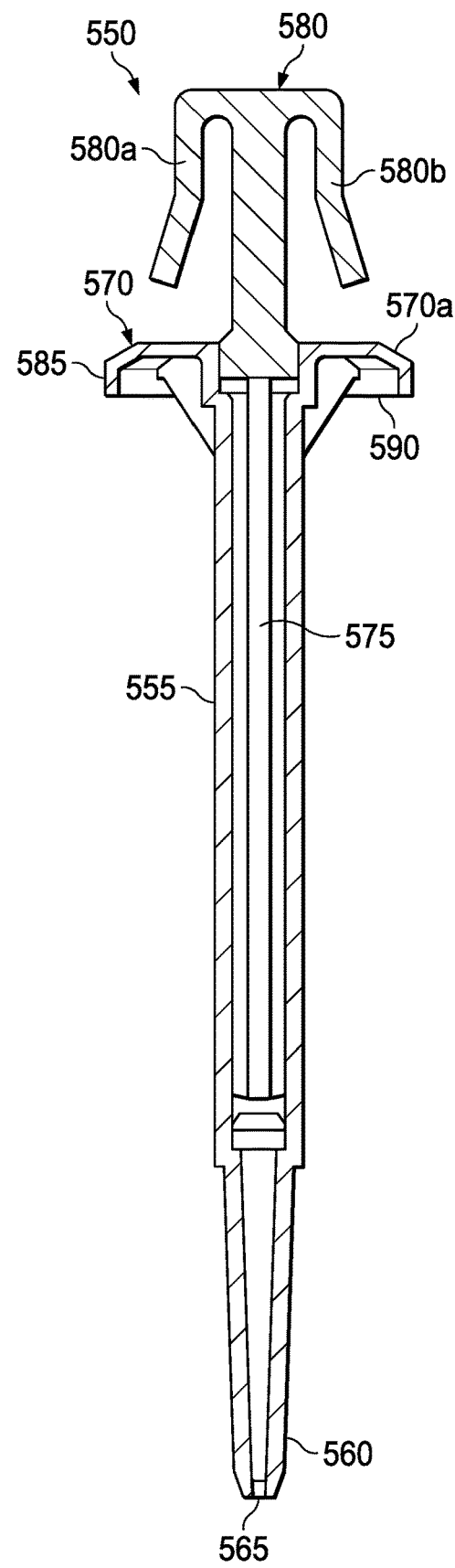
FIG. 7A
FIG. 7B

POSITIVE DISPLACEMENT PIPETTE SYRINGE IDENTIFICATION SYSTEM

TECHNICAL FIELD

Exemplary embodiments of the general inventive concept are directed to a handheld powered positive displacement pipette and pipette assembly, including novel syringes for said pipette, and associated mechanisms for the releasable retention, ejection, and possible automatic identification of said syringes.

BACKGROUND

As would be understood by one of skill in the art, pipettes are generally of either air displacement or positive displacement design. In contrast to an air displacement pipette in which a cushion of air separates aspirated liquid from the pipette piston, a positive displacement pipette is designed for direct contact between the pipette piston and the aspirated liquid.

The positive displacement pipette design eliminates potential air displacement pipette inaccuracies that may result from the effects of different liquid properties and/or environmental conditions on the air cushion of the air displacement pipette. For example, altitude changes, evaporation and other conditions to which an air displacement pipette may be subjected can affect air displacement pipette accuracy.

While a positive displacement pipette can provide the aforementioned advantages over an air displacement pipette, known positive displacement pipettes have their own shortcomings. One such shortcoming has traditionally been the inability of known positive displacement pipettes to provide accurate, non-contact dispensing of very small liquid volumes, including volumes below 1 µl. More specifically, when dispensing very small liquid volumes using known positive displacement pipettes there is a tendency for some amount of liquid to adhere to the inside of the pipette tip after the dispensing stroke, which then requires subsequent physical contact ("touch-off") of the pipette tip with the liquid receiving vessel to discharge said adhering liquid from the pipette tip.

Additionally, direct contact between the piston of a positive displacement pipette and the liquid of interest during normal use means that the piston cannot be reused. Consequently, positive displacement pipettes typically use a "consumable" in the form of a disposable syringe that includes not only a hollow barrel (capillary) with a tip portion, but also a piston that resides and seals within the capillary and is reciprocatable within the capillary by the pipette to aspirate and dispense a desired amount of a liquid of interest while the capillary and piston are releasably attached to the pipette. After the pipetting operation is complete, the entire syringe is normally removed from the positive displacement pipette and discarded.

The complexity associated with the insertion, retention and ejection of a positive displacement pipette syringe is greater than that associated with a typical air displacement pipette tip, which is far more simplistic in construction and commonly held in place on the dispensing end of an air displacement pipette body by mere friction. In a positive displacement pipette, the syringe must be securely retained on the pipette body until deliberately ejected, while the piston is simultaneously properly positioned within the pipette for releasable engagement and reciprocation by an aspiration/dispensing mechanism of the pipette.

There is an existing need for a positive displacement pipette that can provide accurate and repeatable non-contact dispensing of various volumes of liquid, including very small liquid volumes. There is also an existing need for a positive displacement pipette having an improved mechanism by which syringes may be easily and reliably installed to, releasably retained by, and ejected from the pipette. Exemplary positive displacement pipettes according to the general inventive concept, and various features of said exemplary positive displacement pipettes, satisfy these needs.

SUMMARY

An exemplary embodiment of a handheld, powered positive displacement pipette according to the general inventive concept will generally include a substantially hollow body that is preferably shaped for ergonomic gripping by a user and acts as a housing for the various internal components of the pipette. A proximal end of the body may include a user interface portion, while a distal end of the body is configured for and serves as the connection end for a syringe.

An exemplary pipette will generally further include a motorized drive assembly, a dispensing solenoid assembly, a syringe retention mechanism, a syringe piston grasping mechanism, and a syringe ejection mechanism, all of which are housed within the pipette body. At least some of the aforesaid components may further reside within an internal housing that is also located within the pipette body.

A syringe is releasably installed to the distal end of the pipette for aspirating and dispensing fluids of interest. Syringes may be provided in a number of different volumes. Regardless of the volume, however, each syringe generally includes a generally hollow external barrel (capillary) that may be of tubular shape, or some other shape such as but not limited to an elliptical or obround shape. The capillary includes a tip with an orifice at its distal end, and functions to contain a fluid specimen to be dispensed. At a top of each capillary resides a syringe retention element, which may be an integral part of the capillary. The shape and dimension of the syringe retention elements cooperates with the syringe retention mechanism of the pipette.

Each syringe also includes a piston having a first, fluid-contacting portion that is arranged within the capillary, and a piston head that is connected thereto and resides proximally of the syringe retention element when the piston is located in the capillary. The piston head is configured for releasable engagement with a piston carrier of the syringe piston grasping mechanism of the pipette.

The motorized drive assembly is responsible for setting various positions of the syringe attached to the pipette, for drawing the syringe piston toward the proximal direction of the pipette to aspirate fluid into the syringe, for moving the syringe piston in a distal direction to dispense fluid from the syringe, and for producing a syringe-ejecting movement.

The dispensing solenoid assembly includes an armature that floats within a bore in a solenoid body and is linearly displaceable relative thereto. The armature includes a shaft that extends through an opening in the solenoid body and connects the armature to the piston carrier, which forms a portion of the syringe piston retention mechanism of the pipette and is engaged with the piston head of the syringe piston.

The dispensing solenoid assembly and the syringe piston grasping mechanism reside substantially within a piston carriage, which is coupled to the output of a drive motor of the motorized drive assembly by a lead screw. In one exemplary embodiment, operation of the drive motor may rotate a drive nut that is engaged with the lead screw but restrained from linear displacement, thereby transferring the rotational output of the motor into a linear displacement of the lead screw and piston carriage, and of components such as the dispensing solenoid that are coupled to the piston carriage. In another exemplary embodiment, operation of the drive motor may rotate the lead screw within a drive nut that is linearly displaceable but rotationally restrained, thereby transferring the rotational output of the motor into a linear displacement of the lead screw, the piston carriage and various components coupled to the piston carriage. In other exemplary embodiments, the lead screw and or drive nut may be replaced with other components that result in a desired, controlled displacement of the piston carriage and various components coupled to the piston carriage.

The dispensing solenoid assembly of an exemplary pipette is configured to, depending on the selected dispensing volume and dispensing mode, produce a pulsed dispensing of a selected volume of fluid on its own or to assist the motorized drive assembly with the dispensing function by ensuring that all of each selected dispensing volume is actually dispensed from the syringe without the need to touch-off the syringe tip against a sample-receiving vessel. More specifically, energizing the solenoid body (coil) produces a rapid and forceful displacement of the solenoid armature toward the distal end of the pipette, thereby causing a like rapid movement of the piston carrier and syringe piston, and expelling a jet of fluid from the syringe tip. The general concept of pulsed fluid dispensing relative to a bench top pipette instrument may be reviewed in European Patent Application EP1344565A1. The displacement of the piston carriage followed by an actuation of the dispensing solenoid assembly can be repeated as desired to dispense multiple aliquots each representing a fraction of the entire liquid volume held by the syringe.

Operation of the motorized drive assembly and the dispensing solenoid assembly is governed by a controller that receives instruction signals from user inputs and/or from internal programming. The controller also receives position information signals from an encoder.

A selected syringe is securely but releasably retained on the pipette by the syringe retention mechanism and the syringe piston is coupled to the solenoid armature via the piston carrier of the syringe piston grasping mechanism as well as to the motorized drive system.

Once an aspiration and dispensing operation is complete, the syringe ejection mechanism is operative to decouple the syringe retention element of the syringe from the syringe retention mechanism and to decouple the syringe piston head from the piston carrier. The motorized drive system then drives the piston carriage toward the distal end of the pipette which, via release elements associated with the piston carriage, causes the syringe retention mechanism to release the syringe capillary and the syringe piston grasping mechanism to disengage from the syringe piston head, whereafter the syringe will be automatically ejected from the pipette.

Various dispensing operations using an exemplary pipette may be accomplished in an automatic mode or via a manual mode. A user is able to access and selectively initiate a desired automatic pipetting program through the user interface portion of the pipette.

Auto mode dispensing may encompass a number of different and selectable dispensing procedures. These dispensing procedures may result, for example: in aspiration of a full syringe volume of fluid, followed by dispensing of the entirety of the aspirated fluid volume in one dispensing operation; in aspiration of some volume of fluid into the syringe, followed by dispensing of the aspirated fluid in multiple doses of equal volume; in aspiration of some volume of fluid into the syringe, followed by dispensing of the aspirated fluid in multiple doses of variable volume; or in aspiration of some volume of fluid into the syringe, followed by dispensing of the aspirated fluid in multiple doses of equal or variable volume until some portion (e.g., 50%) of the aspirated volume has been dispensed, and then performing another aspiration operation. A dispensing operation may also be performed by a user in a manual mode rather than by the controller of the pipette operating in auto mode.

Performance of a titration procedure may also be possible. A titration program of an exemplary pipette may include a titrated volume counter that indicates the volume of titrant that has been dispensed, and the counter may be resettable to allow for multiple titration operations from a single aspirated volume of titrant.

An exemplary pipette may also include fluid viscosity detection capability, such as by, for example and without limitation, providing the pipette with appropriate circuitry or other means for monitoring an increase in current draw of the motorized drive assembly motor required to move the syringe piston relative to the syringe capillary during an aspiration or dispensing operation; through use of a provided load cell that measures the force required to move the syringe piston relative to the syringe capillary during an aspiration or dispensing operation; by way of a mechanical spring; or via another technique that would be understood by one of skill in the art. The value of the current draw may be used to categorize the viscosity of the fluid, and the pipette controller may adjust the dispensing operation parameters of the pipette based on the identified fluid viscosity category.

An exemplary pipette may be further provided with an automatic syringe identification system. Such a system would allow the controller of the pipette to automatically select the appropriate operating parameters for the given syringe volume, thereby simplifying the setup process and possibly eliminating operator error associated with mistakenly identifying the volume of a syringe being used. Such a system may be effectuated, for example, by associating each syringe volume with a different color, placing an area of corresponding color on the syringe, locating in the pipette a color sensor that is configured and located to image the colored areas on the syringes, and transmitting imaging data from the color sensor to the pipette controller. The signal to the pipette controller is indicative of the color of the colored area on the syringe, and the controller is programmed to analyze the signal and to resultingly identify the volume of the installed syringe.

An exemplary pipette according to the general inventive concept is able to accurately and repeatably dispense fluid doses of sub-microliter volume through volumes of milliliters or more. The ability to automatically dispense selected volumes of fluids of interest without the need to touch off the syringe tip means that the dispensing operation is also user independent, and therefore insulated from possible user-introduced error. These are significant improvements over the capabilities of known positive displacement pipettes.

Other aspects and features of the general inventive concept will become apparent to those of skill in the art upon review of the following detailed description of exemplary embodiments along with the accompanying drawing figures.

BRIEF DESCRIPTION OF THE DRAWINGS

In the following descriptions of the drawings and exemplary embodiments, like reference numerals across the several views refer to identical or equivalent features, and:

FIG. 5A is cross-sectional side view of the exemplary pipette assembly of FIG. 2, with various internal components of the pipette and a piston of the syringe shown in an aspirating position;

FIG. 5B is an enlarged transparent view of a portion of the pipette of FIG. 5A;

FIGS. 7A-7B are a perspective view and a cross-sectional side view, respectively, of an exemplary 1.0 ml syringe for use with an exemplary inventive pipette;

DETAILED DESCRIPTION OF THE EXEMPLARY EMBODIMENTS

Figure 1:
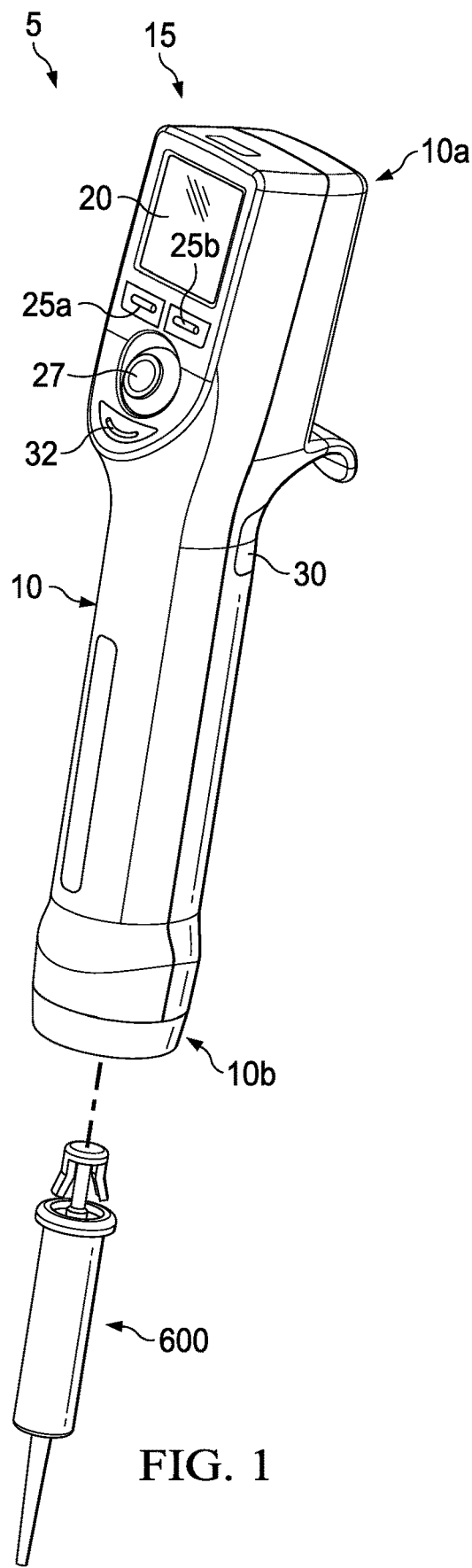
FIG. 1 is a perspective view of an exemplary embodiment of a motor-driven positive displacement pipette according to the general inventive concept, and includes a syringe shown prior to insertion into the pipette.
Figure 2:
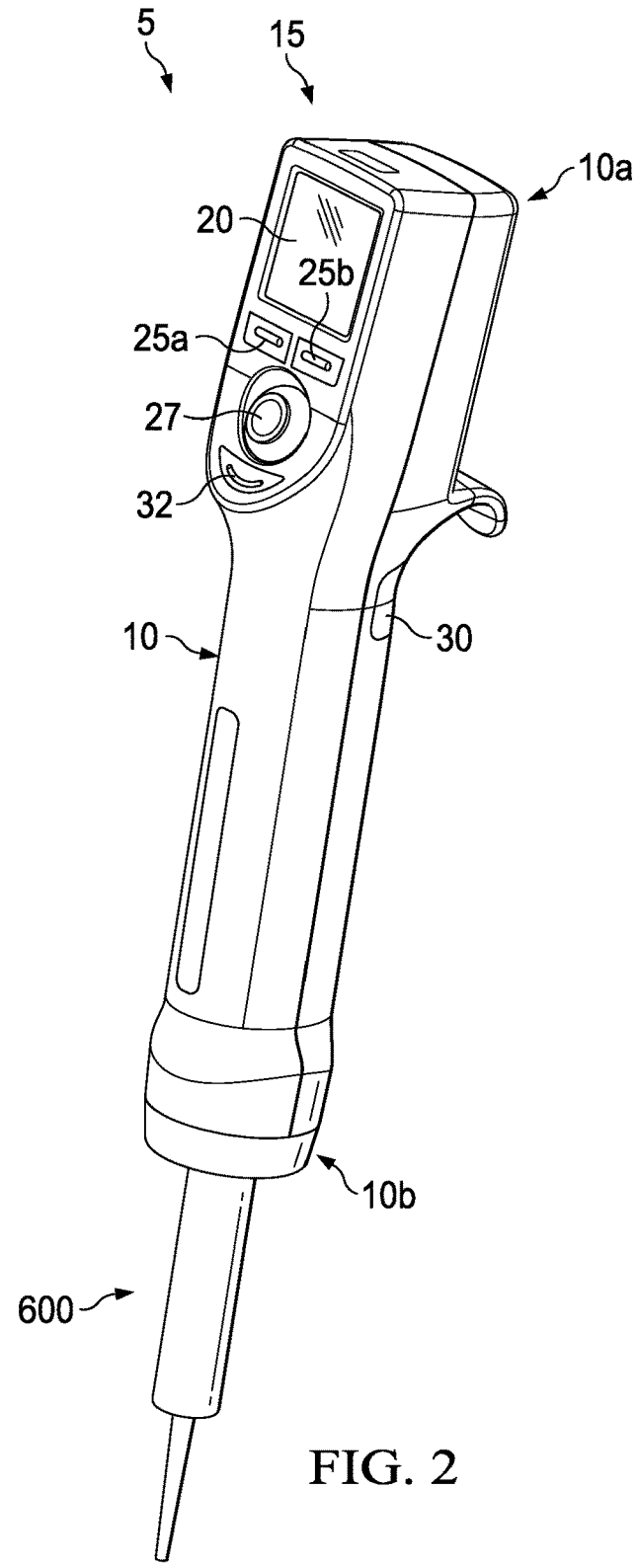
FIG. 2 shows an assembly of the exemplary pipette of FIG. 1 with the syringe installed into and retained by the pipette.

FIG. 1 depicts one exemplary embodiment of a handheld, motor-driven positive displacement pipette 5 (hereinafter "pipette" for brevity) according to the general inventive concept. Also shown in FIG. 1 is a consumable in the form of an exemplary disposable syringe 600 (see FIGS. 8A-8B) that is installed to the pipette in order to perform a pipetting operation. Various exemplary syringes for use with exemplary inventive pipettes are shown in FIGS. 6A-10B and described in more detail below. FIG. 2 shows an assembly of the pipette 5 and syringe 600 of FIG. 1.

The exemplary pipette 5 of FIGS. 1-2 includes a body 10 for gripping by a user. The body 10 is generally a substantially hollow structure that also serves as an external housing for various internal components of the pipette 5. The body 10 may be of different shape and/or size in other embodiments, although the shape and size will typically be dictated to at least some extent by the ergonomics of use.

Figure 3:
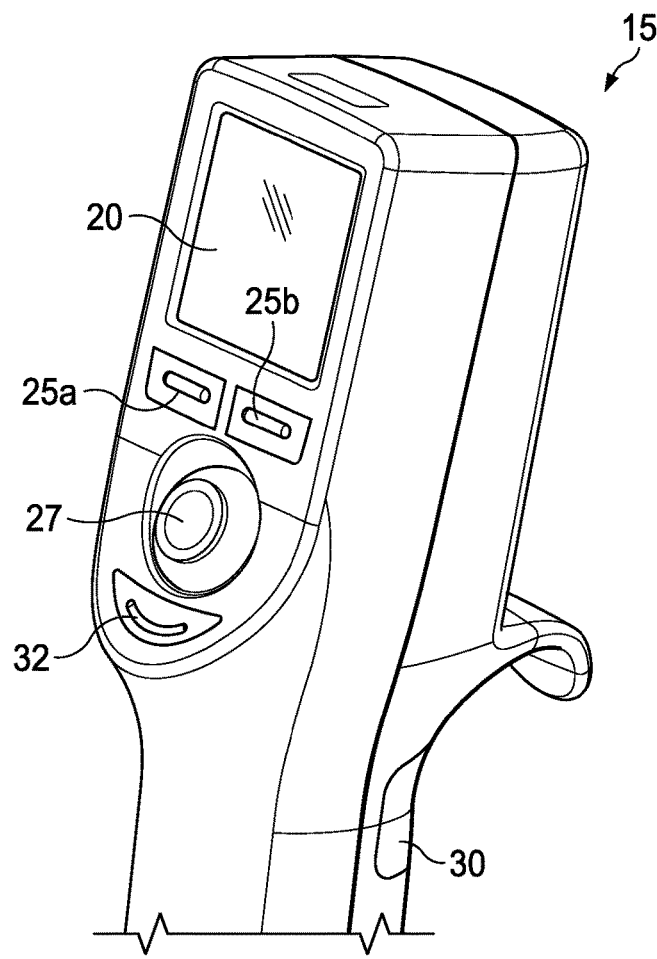
FIG. 3 is enlarged view of a user end of the exemplary pipette of FIGS. 1-2.
Figure 4:
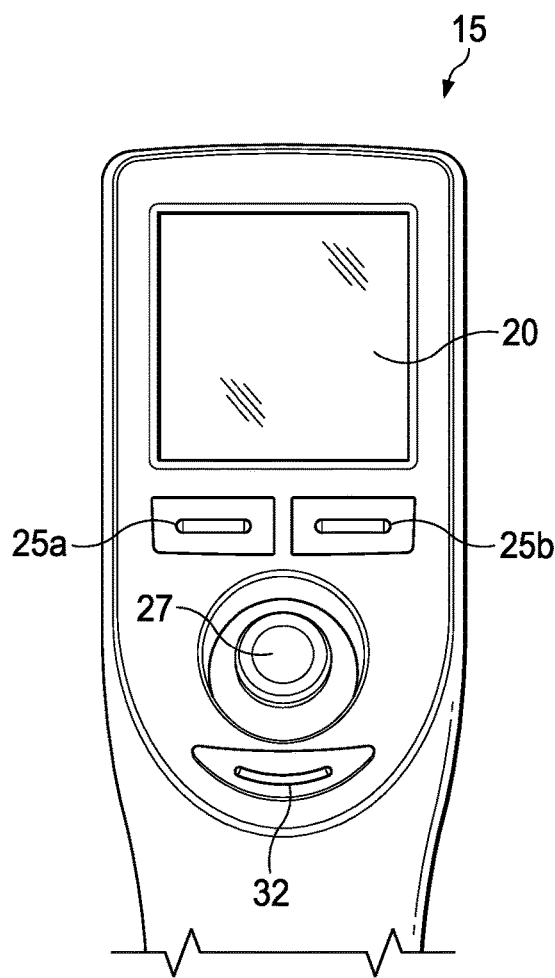
FIG. 4 represents an exemplary user interface provided on the user end of an exemplary pipette according to the general inventive concept.

The body 10 further includes a proximal (user) end 10a and distal end 10b that serves as the connection end for the syringe 600. In this example, the proximal end 10a of the body 10 includes a user interface portion 15. Referring also to FIGS. 3-4, it may be observed that the user interface portion 15 of this exemplary pipette 5 further includes a display 20 and various actuators such as input/selection buttons 25a, 25b, and a joystick 27 that allow a user to observe and select pipette functions, observe and change pipette settings and engage in various other interactions with a programmable controller of the pipette, as would be understood by one of skill in the art. In this exemplary embodiment of the pipette 5, a trigger switch 30 is also provided for initiating pipette operation, and an eject button 32 is provided for initiating a syringe ejection operation.

FIG. 5A is a cross-sectional side view of the exemplary pipette 5 and syringe 600 assembly of FIG. 2, which reveals the various internal components of the pipette that are concealed by the body 10. As may be observed, the exemplary pipette 5 includes, among other components, a motorized drive assembly 40, a dispensing solenoid assembly 250, a syringe retention mechanism 150 and syringe piston grasping mechanism 200, all of which are described in more detail below. The assembly of FIG. 5A also includes the syringe 600, which is releasably retained by the syringe retention mechanism 150 of the pipette 5 and is shown in a post-aspiration and pre-dispensing position. An enlarged and transparent view of a portion of the proximal end 10a of the pipette body 10 is shown in FIG. 5B, and reveals additional pipette components such as a printed circuit board and various electronic components, including motor control circuitry comprising a controller 90.

Figure 6A:
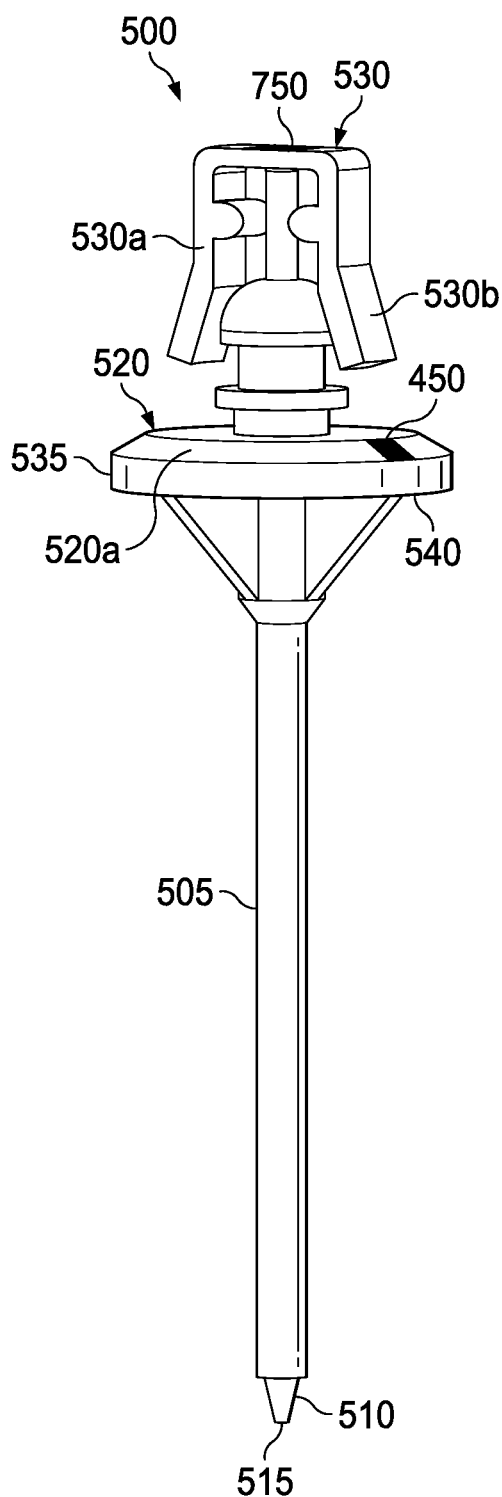
FIGS. 6A-6B are a perspective view and a cross-sectional side view, respectively, of an exemplary 0.1 ml syringe for use with an exemplary inventive pipette.
Figure 6B:
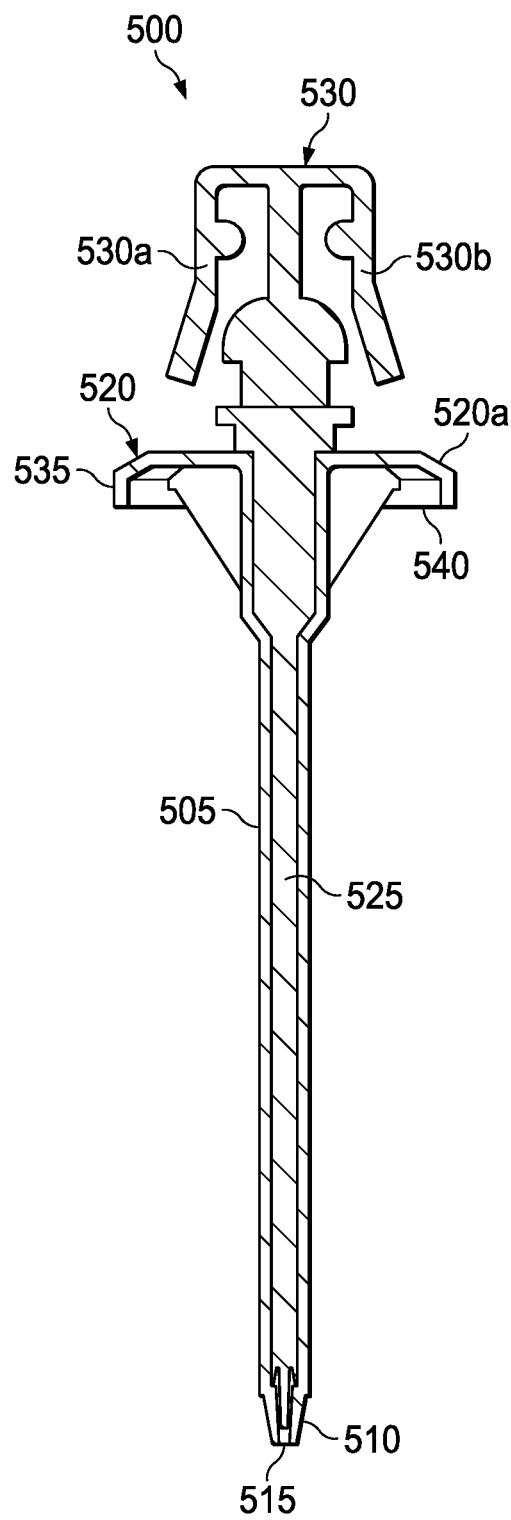
Figure 6C:
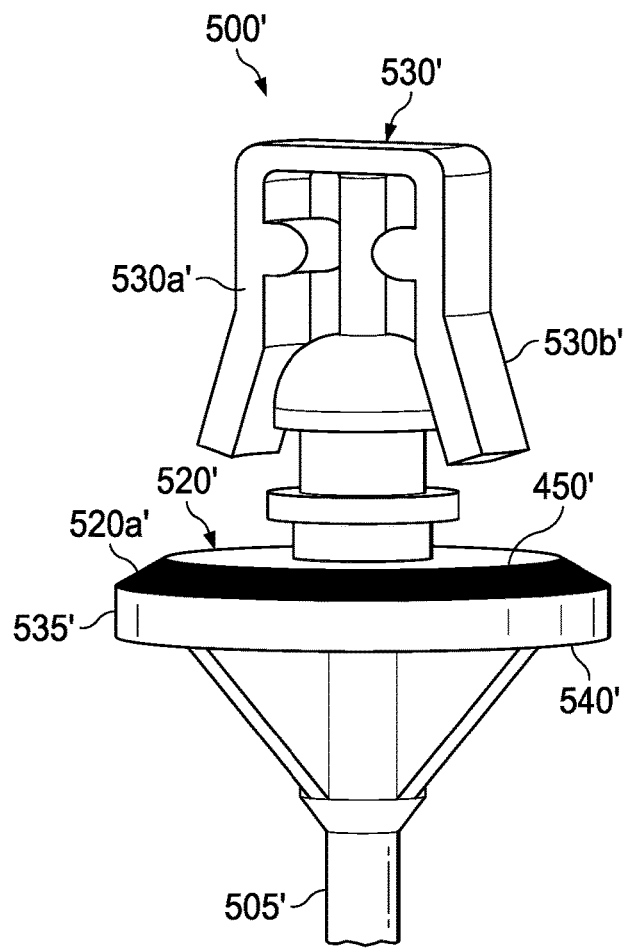
FIG. 6C is an enlarged view of a portion of the 0.1 ml syringe shown in FIG. 6A, illustrating an alternative embodiment of a colored marking on a syringe retention element thereof.
Figure 7C:
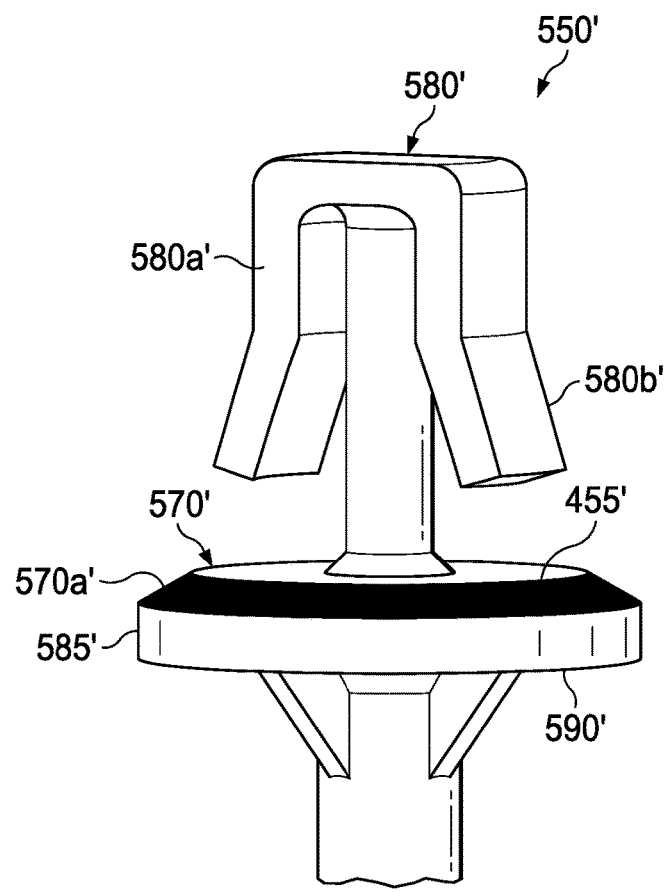
FIG. 7C is an enlarged view of a portion of the 1.0 ml syringe shown in FIG. 7A, illustrating an alternative embodiment of a colored marking on a syringe retention element thereof.
Figure 8A:
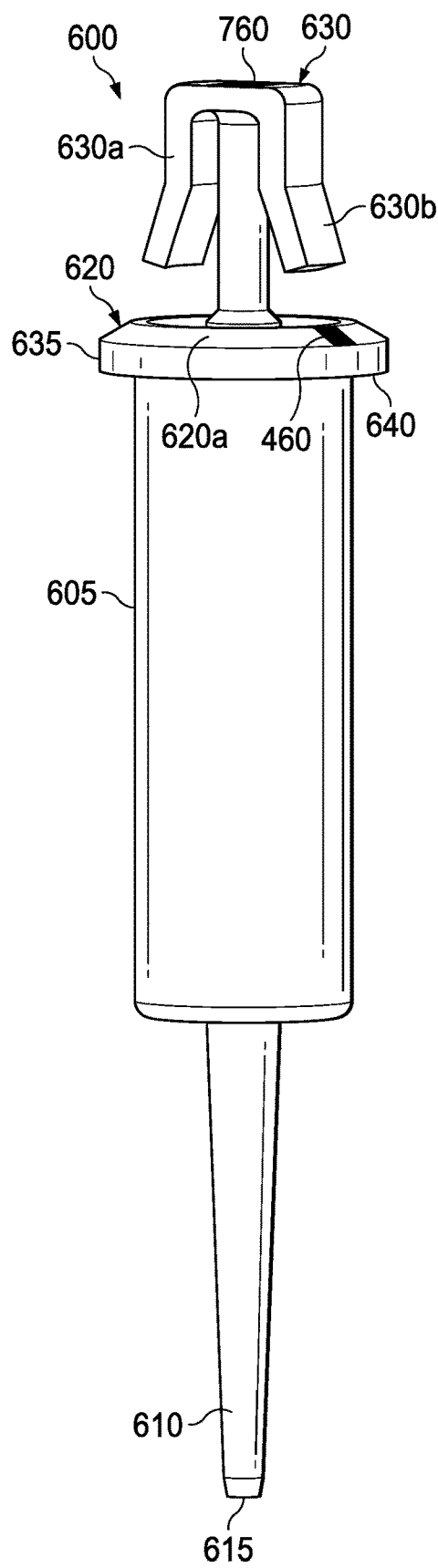
FIGS. 8A-8B are a perspective view and a cross-sectional side view, respectively, of an exemplary 10 ml syringe for use with an exemplary inventive pipette.
Figure 8B:
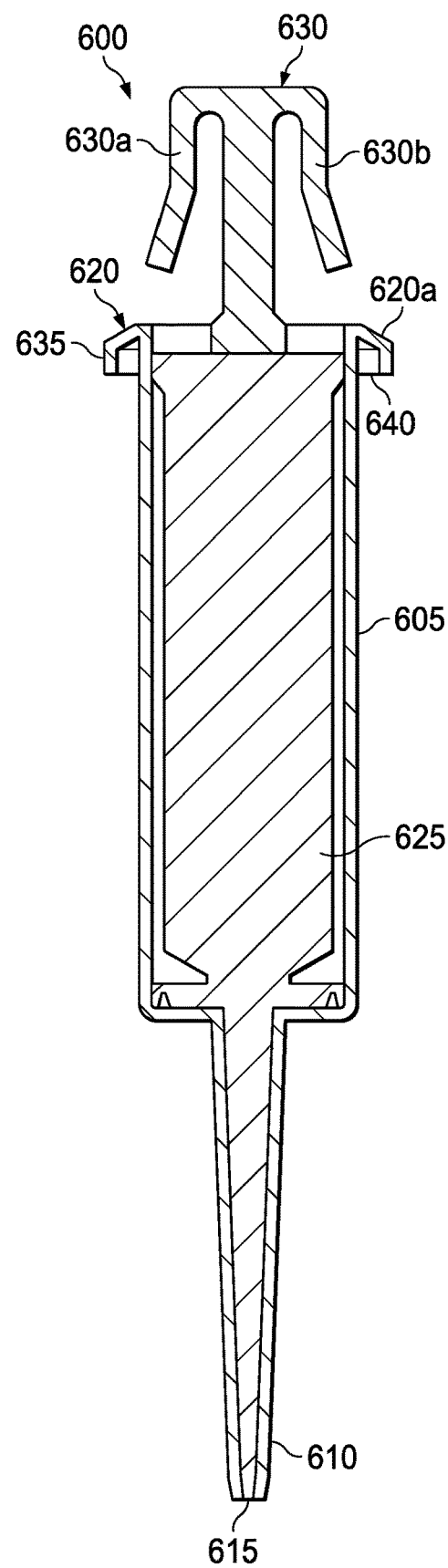
Figure 8C:
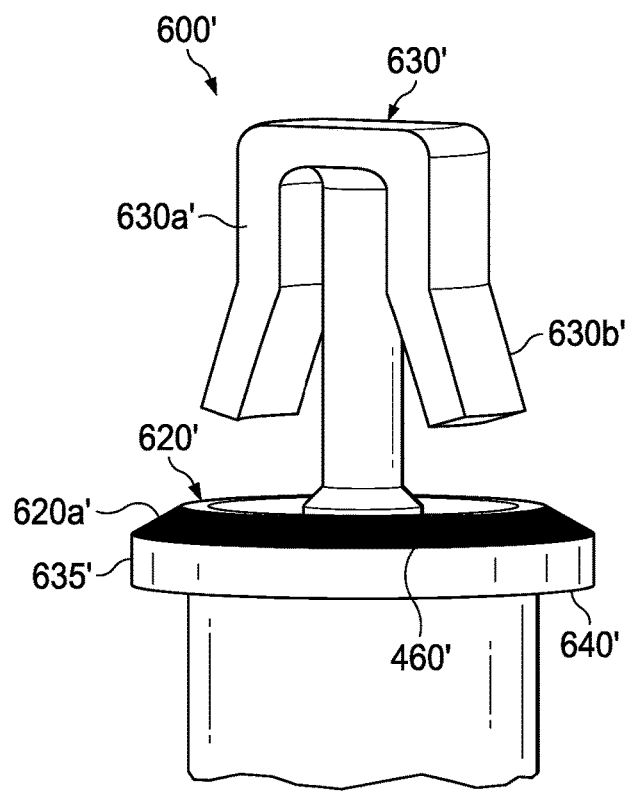
FIG. 8C is an enlarged view of a portion of the 10 ml syringe shown in FIG. 8A, illustrating an alternative embodiment of a colored marking on a syringe retention element thereof.
Figure 9C:
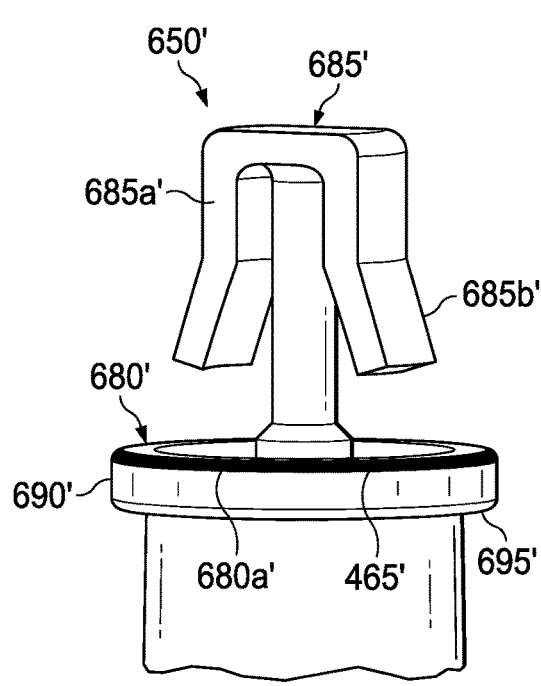
FIG. 9C is an enlarged view of a portion of the 25 ml syringe shown in FIG. 9A, illustrating an alternative embodiment of a colored marking on a syringe retention element thereof.
Figure 10C:
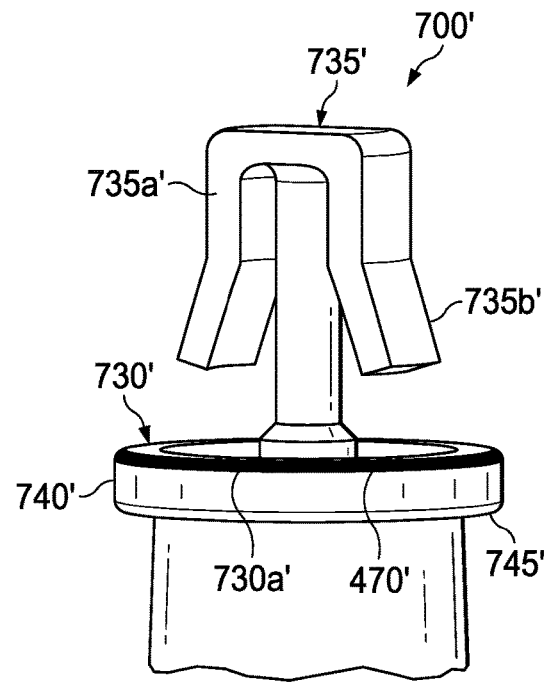
FIG. 10C is an enlarged view of a portion of the 50 ml syringe shown in FIG. 10A, illustrating an alternative embodiment of a colored marking on a syringe retention element thereof.
Figure 9A:
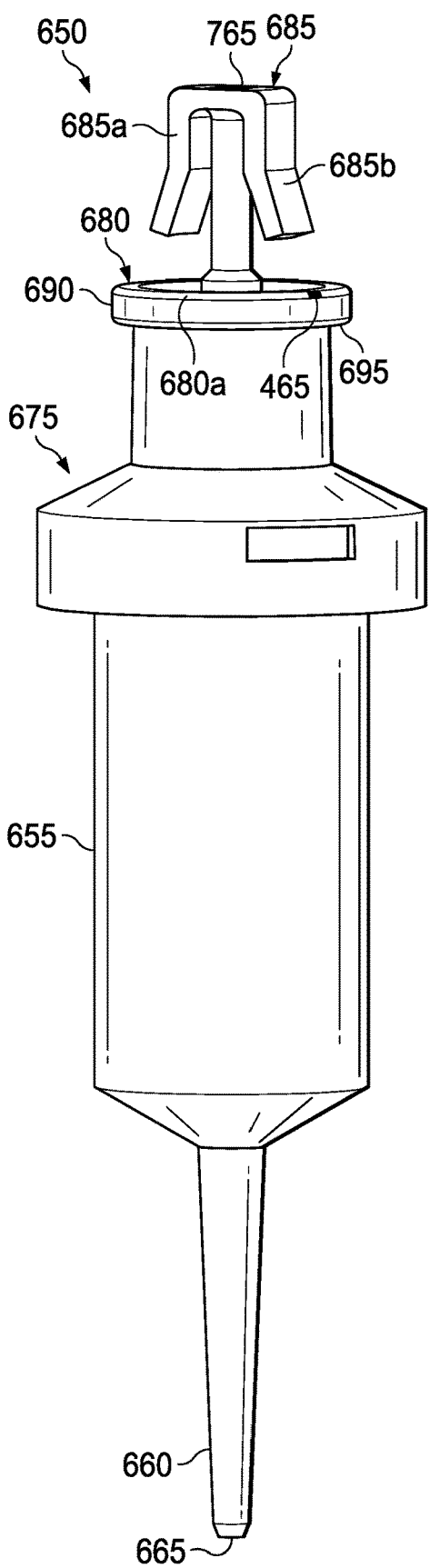
FIGS. 9A-9B are a perspective view and a cross-sectional side view, respectively, of an exemplary 25 ml syringe for use with an exemplary inventive pipette.
Figure 9B:
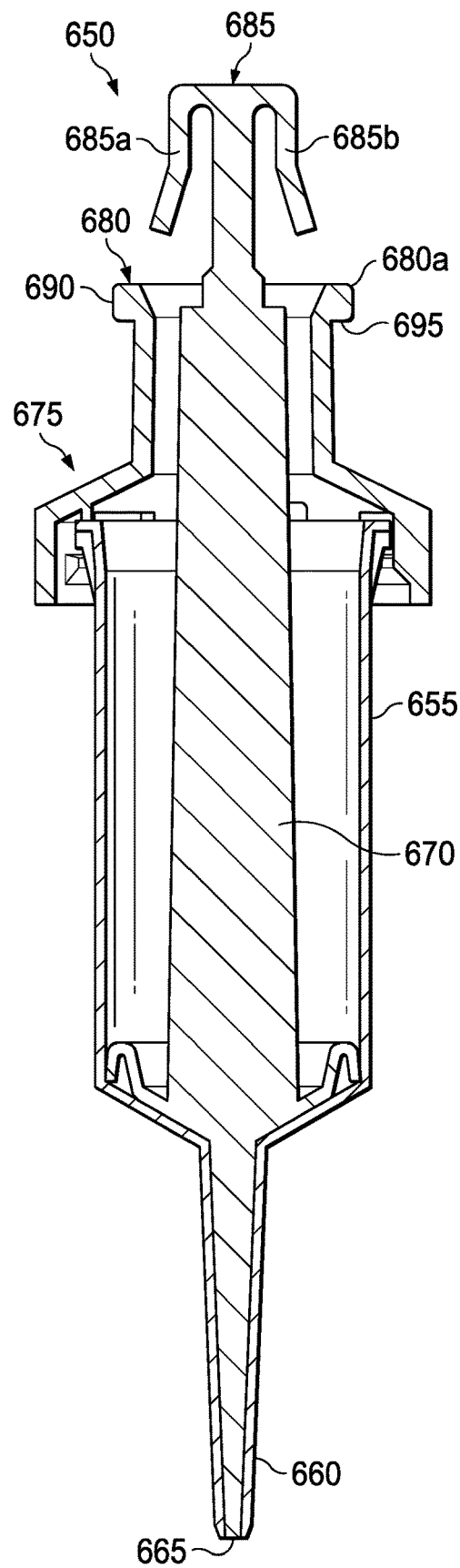
Figure 10A:
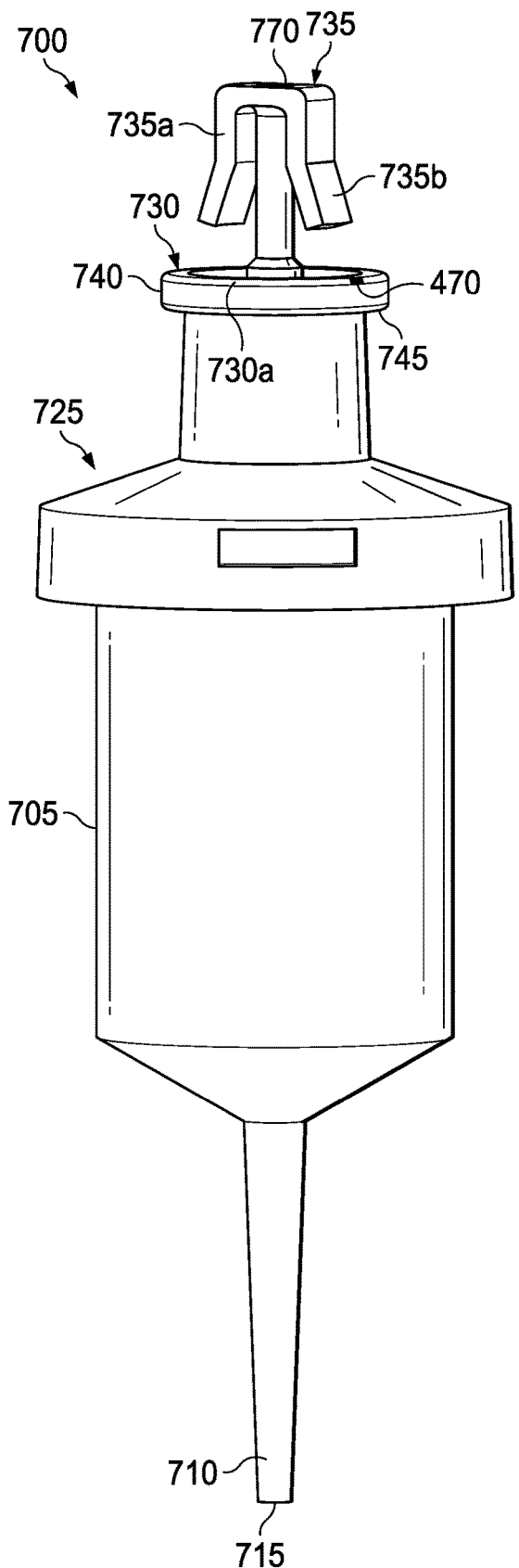
FIGS. 10A-10B are a perspective view and a cross-sectional side view, respectively, of an exemplary 50 ml syringe for use with an exemplary inventive pipette.
Figure 10B:
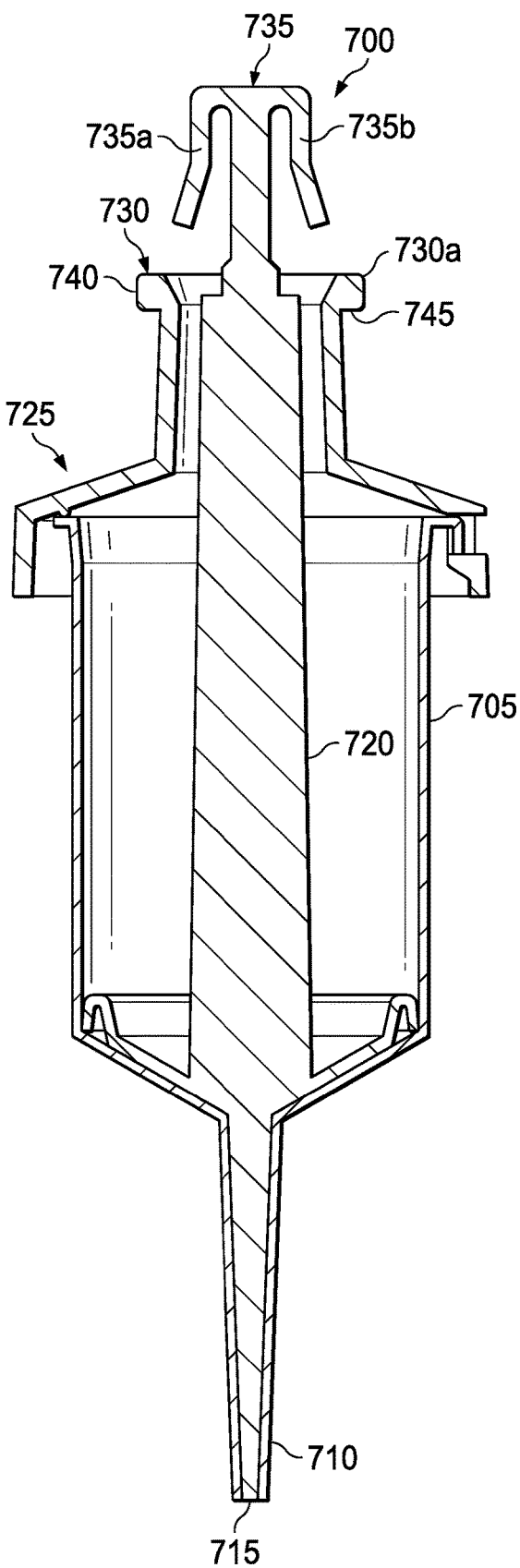

A variety of exemplary syringes that are usable with an exemplary pipette according to the general inventive concept are represented in the perspective and cross-sectional elevation views of FIGS. 6A-10B. The exemplary syringes 500-600 are arranged in order of increasing of volume, with FIGS. 6A-6B representing an exemplary syringe 500 having a volume of 0.1 ml, FIGS. 7A-7B representing an exemplary syringe 550 having a volume of 1.0 ml, FIGS. 8A-8B representing an exemplary syringe 600 having a volume of 10 ml, FIGS. 9A-9B representing an exemplary syringe 650 having a volume of 25 ml, and FIGS. 10A-10B representing an exemplary syringe 700 having a volume of 50 ml. Thus, while the exemplary syringe 600 of FIGS. 8A-8B has been arbitrarily selected as the syringe component of an exemplary pipette and syringe assembly for purposes of illustration, it should be understood that an exemplary inventive pipette is usable with a number of different syringes to accurately and repeatably dispense samples across a wide volume range.

Each of the exemplary syringes 500, 550, 600 shown in FIGS. 6A-8B includes an external barrel, referred to herein as a capillary 505, 555, 605, which is of generally hollow and tubular construction and functions to contain the fluid specimen to be dispensed. A distal end of each capillary 505, 550, 605 includes a tip 510, 560, 610 having an orifice 515, 565, 615 through which fluid previously aspirated into the capillary may be dispensed. A top of each capillary 505, 555, 605 forms a syringe retention element 520, 570, 620 of like shape and dimension. The shape and dimension of the syringe retention elements 520, 570, 620 allows for engagement thereof by the syringe retention mechanism 150 located in the pipette 5. For example, in particular syringe embodiments shown, each syringe retention element 520, 570, 620 includes a circumferential edge 535, 585, 635 and a lower face 540, 590, 640 that may be engaged by elements of the syringe retention mechanism 150.

Each syringe 500, 550, 600 also includes a piston 525, 575, 625 (sometimes also referred to as a plunger) having a first, fluid-contacting portion that is concentrically arranged within the capillary 505, 555, 605 for aspirating and dispensing fluid, a head 530, 580, 630 portion that resides proximally of the syringe retention element 520, 570, 620, and a connecting portion that passes through an aperture in the syringe retention element to connect the piston head with the fluid-contacting portion. The piston heads 530, 580, 630 of the exemplary syringes 500, 550, 600 shown herein are substantially bell-shaped, and include opposing arms 530a-530b, 580a-580b, 630a-630b that permit at least some degree of elastic deformation thereof. Other piston head shapes and other numbers of arms may be possible in other embodiments.

When a syringe 500, 550, 600 is properly installed to the pipette 5, the syringe is retained in a stationary position by engagement of the syringe retention element 520, 570, 620 of the syringe and the syringe retention mechanism 150 of the pipette, and a head 530, 580, 630 portion of the piston 525, 575, 625 is engaged by the piston grasping mechanism 200 of the pipette, such that the fluid-contacting portion of the piston is reciprocatable within the capillary 505, 555, 605 by the pipette. The syringes 500, 550, 600 are ejectable from the pipette 5 after use, as described in more detail below.

The exemplary syringes 650, 700 shown respectively in FIGS. 9A-9B and 10A-10B are designed for use in the pipetting of larger fluid volumes. In these exemplary syringe embodiments, a capillary 655, 705 having a tip 660, 710 with an orifice 665, 715 is again included, and a piston 670, 720 is again arranged to reciprocate within the capillary. However, unlike the exemplary syringe embodiments 500, 550, 600 depicted in FIGS. 6A-8B, the capillaries 655, 705 of the syringes 650, 700 have open tops (proximal ends) and do not include a syringe retention element. Instead, each syringe 650, 700 includes a reusable adaptor 675, 725 for connecting the syringe to the pipette 5.

Each adaptor 675, 725 has an open distal end that is dimensioned to receive the proximal end of the syringe 650, 700. Retention elements at the proximal end of the capillary 655, 705 and in the distal end of the adaptor 675, 725 cooperate to secure the capillary to the adaptor. The proximal end of the adaptor 675, 725 forms a syringe retention element 680, 730 that is shaped and dimensioned to engage with the syringe retention mechanism in the pipette 5. For example, in particular syringe embodiments shown, each syringe retention element 680, 730 includes a circumferential edge 690, 740 and a lower face 695, 745 that may be engaged by elements of the syringe retention mechanism 150.

Each syringe 650, 700 includes a piston 620, 720 having a first, fluid-contacting portion that is concentrically arranged within the capillary 655, 705 for aspirating and dispensing fluid, a head 685, 735 portion that resides proximally of the syringe retention element 680, 730 of the adaptor 675, 725, and a connecting portion that passes through an aperture in the syringe retention element to connect the piston head with the fluid-contacting portion. The piston heads 685, 735 of the exemplary syringes 650, 700 shown herein are again substantially bell-shaped, and include opposing arms 685a-685b, 735a-735b that permit at least some degree of elastic deformation thereof. Other piston head shapes and other numbers of arms may be possible in other embodiments.

When a large volume syringe 650, 700 is properly installed to the pipette 5, the syringe is retained in a stationary position by engagement of the syringe retention element 680, 730 of the adaptor 675, 725 and the syringe retention mechanism 150 of the pipette, and the piston head 685, 735 is engaged by the piston grasping mechanism 200 of the pipette, such that the fluid-contacting portion of the piston is reciprocatable within the capillary 655, 705 by the pipette. The syringes 650, 700 are ejectable from the pipette 5 after use, as described in more detail below.

It is to be understood that the syringes of FIG. 6A through FIG. 10B have been provided for purposes of illustration only, and variations are certainly possible. For example, and without limitation, the piston head and the piston of a given syringe may be separate, engageable elements, rather than integral parts of a single element as shown ad described herein.

Likewise, although only the exemplary larger volume syringes 650, 700 of FIGS. 9A-10B are shown and described as employing an adapter with an open-top capillary, it is equally possible that the smaller volume syringes 500, 550, 600 of FIGS. 6A-8B may be of a like design and also include an adapter. When a given syringe includes an adapter, the adapter may be a reusable component rather than a consumable component as will be the remainder of the syringe in most syringe embodiments.

Figure 11:
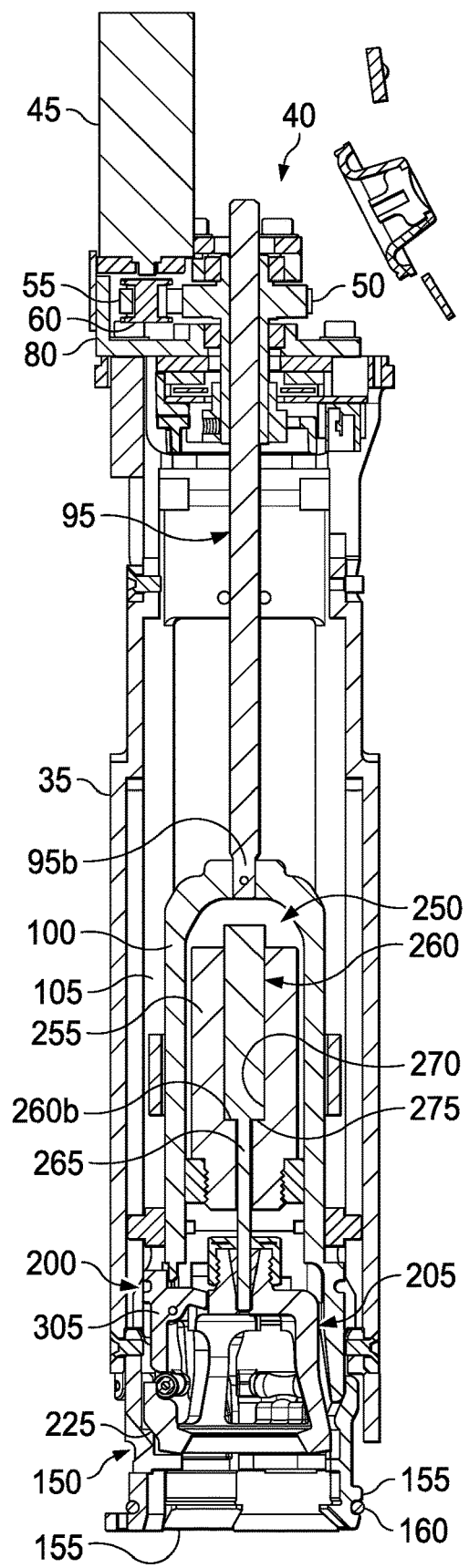
FIG. 11 is a cross-sectional side view of the exemplary pipette of FIG. 1A, with a housing portion of the pipette removed to better reveal various internal components of the pipette.

A cross-sectional side view of the exemplary pipette 5 of FIG. 1 is illustrated in FIG. 11, with the body 10 thereof removed to better reveal the various internal components of the pipette. As briefly described above, the pipette 5 can be seen to include a motorized drive assembly 40 at a proximal end, a syringe retention mechanism 150 at a distal end, and a dispensing solenoid assembly 250 and a syringe piston grasping mechanism 200 interposed therebetween. The pipette 5 also includes an internal housing 35 that contains each of the dispensing solenoid assembly 250, the syringe piston grasping mechanism 200 and the syringe retention mechanism 150. The motorized drive assembly 40 is attached to a proximal end of the internal housing 35.

Figure 12:
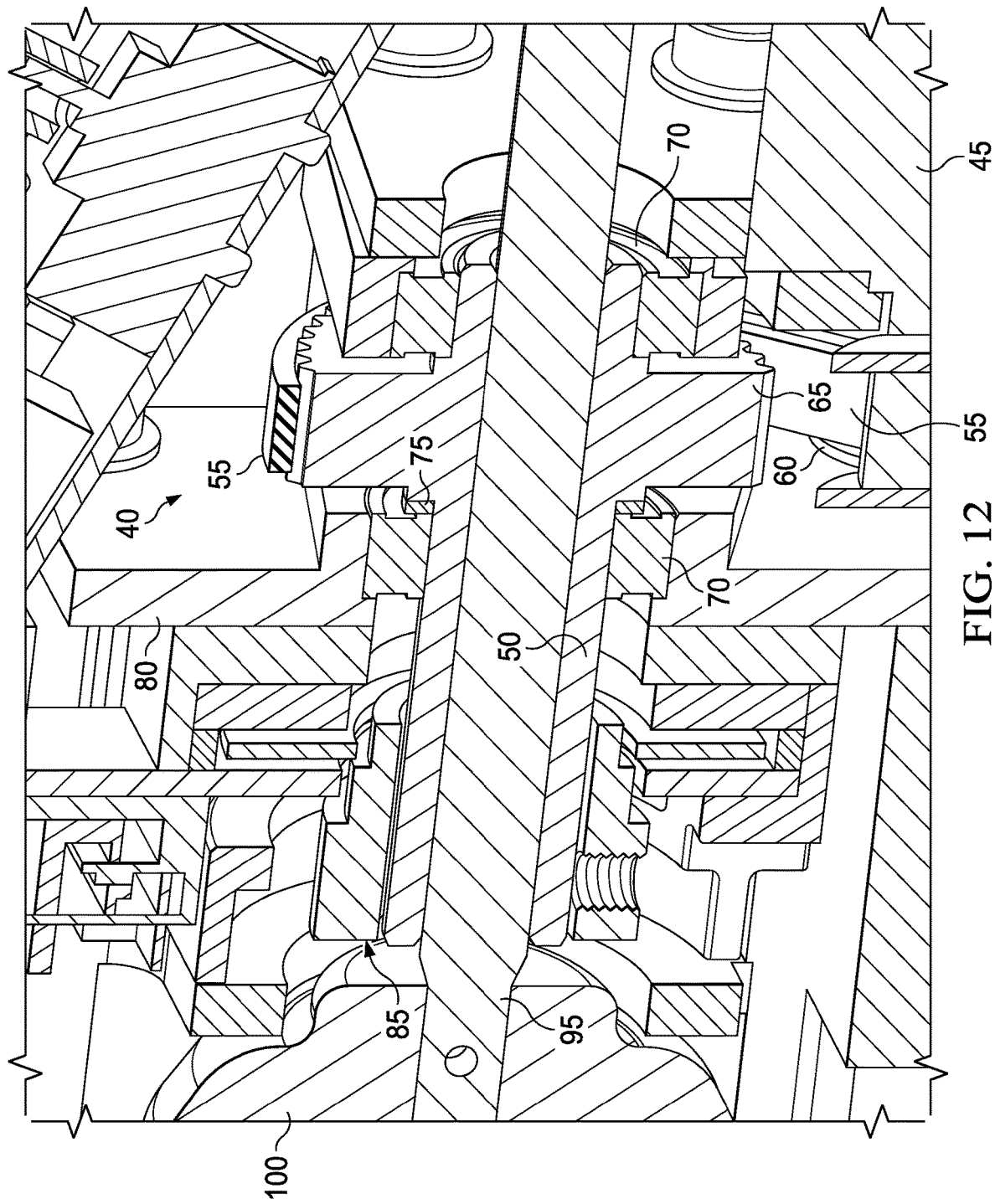
FIG. 12 is an enlarged, cross-sectional perspective view of various internal drive components of the exemplary pipette of FIG. 11.

The motorized drive assembly 40 is responsible for setting various positions of the syringe 600 attached to the pipette 5, for moving the syringe piston in a distal-to-proximal direction to aspirate fluid into the syringe, for moving the syringe piston in a proximal-to-distal direction to dispense fluid from the syringe, and for producing the movement necessary to eject the syringe. Referring also to FIG. 12, it may be observed that in this exemplary pipette 5, the motorized drive assembly 40 includes a drive motor 45 having its output shaft coupled to a rotatable drive nut 50 by a drive belt 55, whereby rotation of the drive nut by the drive motor causes a linear displacement of a lead screw 95 that passes through the drive nut and is in threaded engagement herewith. Other drive schemes may be utilized in other embodiments, such as for example, a direct drive scheme where the output of the drive motor is connected to the lead screw 95 directly by a coupling, or possibly through a speed reduction gear assembly.

In this exemplary motorized drive assembly 40, the drive belt 55 may connect an output pinion 60 affixed to the output shaft of the motor 45 to an input pinion 65 that is coupled to or integral to the drive nut 50. The drive nut 50 may be provided with bearings 70 to facilitate rotation of the drive nut, and the drive nut may also be preloaded with a spring 75 (e.g., wave spring) that will bias the drive nut toward the proximal end of the pipette 5 to help account for any manufacturing (e.g., stack-up) tolerance variations within the motorized drive assembly 40 and to minimize backlash that may otherwise contribute to inaccuracies during a dispensing operation. A mounting block 80 or a similar structure/component may be provided to facilitate mounting of the various components of the motorized drive assembly 40.

The dispensing solenoid assembly 250 is configured to, depending on the selected dispensing volume, dispense the selected volume of fluid on its own or to assist the motorized drive assembly 40 with the dispensing function by ensuring that all of a selected dispensing volume is actually dispensed from the syringe 600 without the need to touch the syringe tip 610 to the sample-receiving vessel (as explained below). The dispensing solenoid assembly 250 includes a solenoid body (coil) 255 that resides within and is coupled to the piston carriage 100, such that the solenoid body moves axially with the piston carriage. The solenoid body 255 includes an axial bore 270 that extends some distance into the solenoid body from the axial end thereof. An armature 260 is concentrically located within the bore 270 and is linearly reciprocatable within the bore and relative to the pipette 5 by a magnetic field that is generated within the bore, as would be understood by one of skill in the art. As the armature 260 floats within the bore 270 as opposed to being coupled to the piston carriage 100 like the solenoid body 255, the armature is not constrained (for some distance) to move linearly with the piston carriage. A bottom wall of the bore 270 acts as an armature hard stop 275 during proximal-to-distal movement of the armature 260. In the exemplary dispensing solenoid assembly 250 shown, the armature 260 includes a shaft 265 that extends through an opening in a bottom wall of the bore 270 toward the distal end of the pipette 5.

Operation of the motorized drive assembly 40 and the dispensing solenoid assembly 250 is governed by the controller 90 (see FIG. 5B). The controller 90 receives instruction signals from user inputs such as the actuators, 25, 30 and/or from internal programming. The controller 90 also receives position information signals from an encoder 85 that is coupled to the drive nut 50.

Rotational motion of the drive nut 50 is converted to linear (axial) motion by the lead screw 95 that passes through the drive nut and is in threaded engagement therewith. Whereas the drive nut 50 is freely rotatable, the lead screw 95 is rotationally constrained but linearly displaceable. Thus, rotation of the drive nut 50 by the drive motor 45 will cause the lead screw 95 to move in a proximal or distal direction along the longitudinal axis of the pipette 5.

The distal end 95b of the lead screw 95 is attached to a proximal end of a piston carriage 100 in a manner that prevents rotation of the lead screw 95. The piston carriage 100 is located in a carriage holder 105 that is mounted within the internal housing 35 so as to be restrained from movement relative thereto. The piston carriage 100 is axially displaceable and reciprocatable within the carriage holder 105, and relative to the longitudinal axis of the pipette 5, but is rotationally restrained.

The dispensing solenoid assembly 250 and the syringe piston grasping mechanism 200 (both described in detail below) reside substantially within the piston carriage 100. Therefore, both the dispensing solenoid assembly 250 and the syringe piston grasping mechanism 200 move with the piston carriage 100 during linear displacement of the piston carriage within the pipette 5.

For proper pipetting, the syringe 600 must be securely retained on the pipette 5 and the motorized drive system 40 of the pipette 5 must be coupled to the syringe piston 625 to reciprocate the syringe piston within the syringe capillary 605. These syringe retention and piston coupling functions are respectively performed by the exemplary syringe retention mechanism 150 and syringe piston grasping mechanism 200 of the pipette 5.

Figure 13:
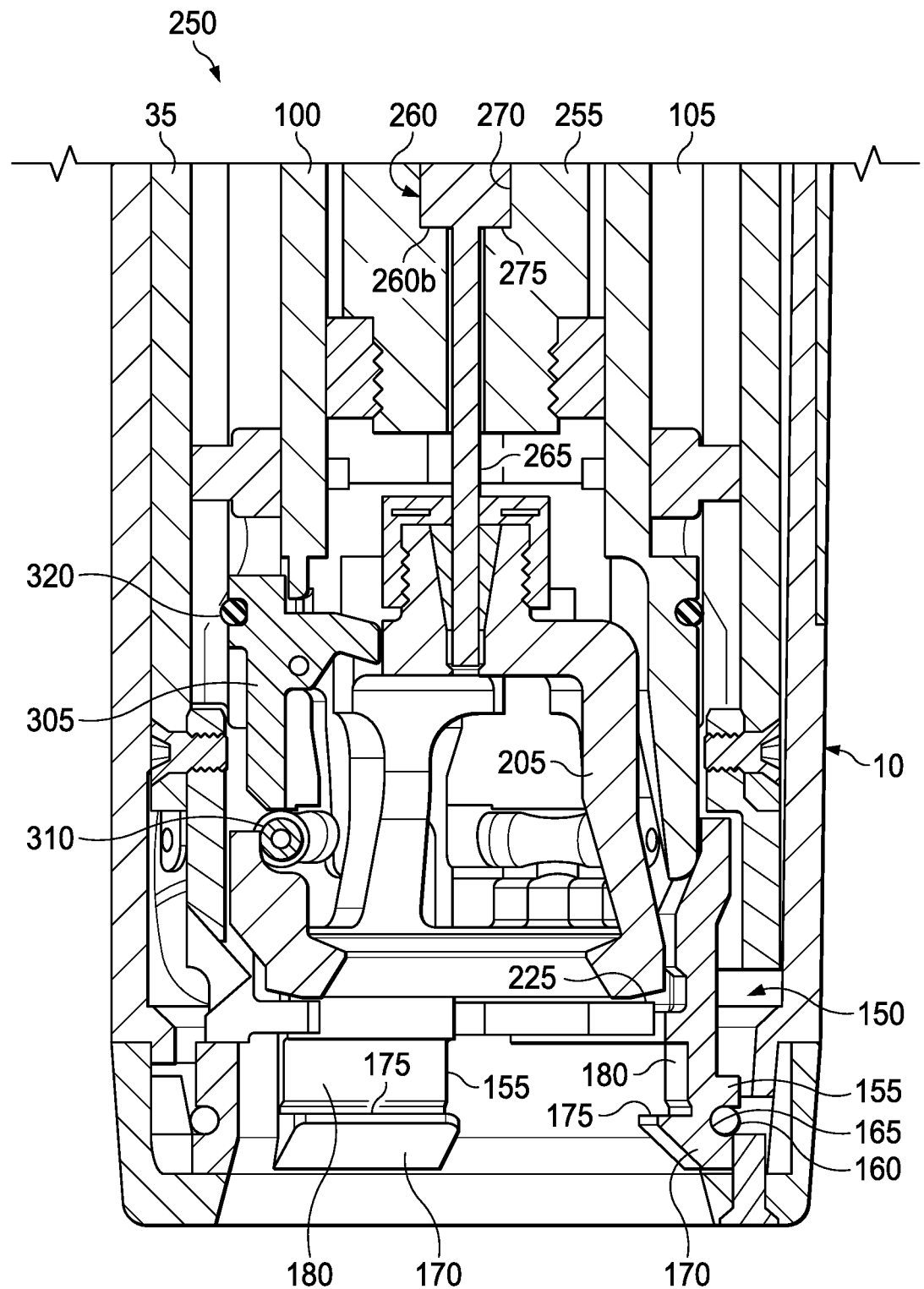
FIG. 13 is an enlarged, cross-sectional view of a distal portion of an exemplary motor-driven positive displacement pipette, showing various internal components that form an exemplary syringe retention mechanism.

A better understanding of the exemplary syringe retention mechanism 150 of the pipette 5 may be obtained by additional reference to FIG. 13, which provides an enlarged cross-sectional view of the distal end of the exemplary pipette 5. The exemplary syringe retention mechanism 150 is shown to include a plurality of spaced apart syringe latching elements 155 that are affixed within the distal end of the pipette 5, such as by a pinned connection 185 to the body 10 (see, e.g., FIG. 20C), so as to be pivotable within some rotational range of motion but restrained against axial movement. In this exemplary pipette 5, there are three syringe latching elements 155 (only two visible in FIG. 11), but a different number of latching elements may be utilized in other embodiments.

The syringe latching elements 155 of the syringe retention mechanism 150 are shown in a closed position in FIG. 11, and are maintained in a normally closed position by an elastic O-ring 160 or similar elastic element that encircles the three syringe latching elements 155 and resides within a slot 165 provided in each latching element. The syringe latching elements 155 are coupled to the piston carrier 205 using a mounting pin 185 (see FIG. 20D), which allows the syringe latching mechanisms to pivot during a syringe insertion procedure as will be more fully explained below.

Each syringe latching element 155 of the syringe retention mechanism 150 also includes a latching hook 170 at its distal end. The latching hooks 170 of the syringe latching elements 155 are designed to engage the syringe retention element on the syringe capillary when the syringe is inserted into the distal end of the pipette 5. For example, with respect to the arrangement of the pipette 5 and the syringe 600 shown in FIG. 5, the latching hooks 170 of the syringe latching elements 155 are designed to engage the syringe retention element 620 (e.g., along the lower face 640) on the syringe capillary 605.

Figure 14A:
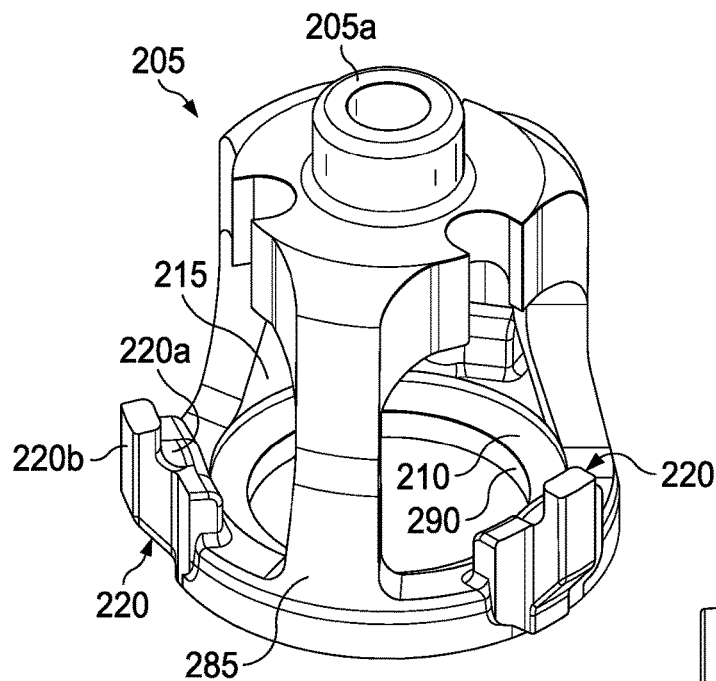
FIG. 14A is a perspective view and FIGS. 14B-14C are elevation views of a piston carrier element of an exemplary syringe piston grasping mechanism.
Figure 14B:
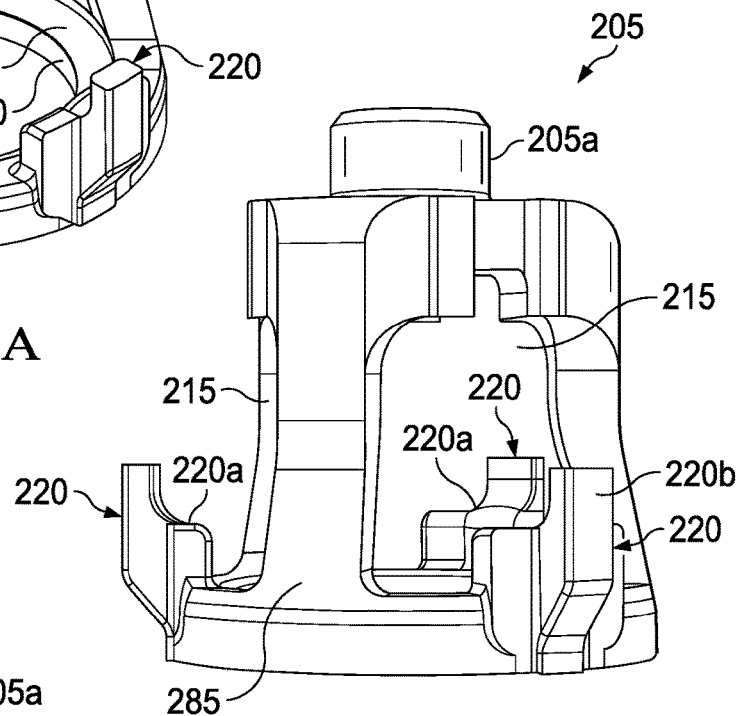
Figure 14C:
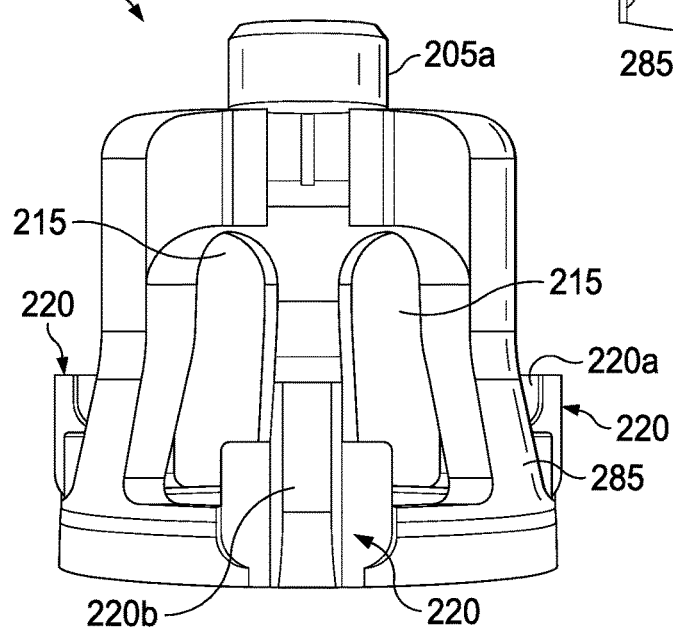

While the syringe retention mechanism 150 secures the capillary of the syringe 600 to the pipette 5 and maintains the capillary in a stationary position relative thereto, the syringe piston grasping mechanism 200 engages and releasably retains the head 630 of the syringe piston 625. To this end, the syringe piston grasping mechanism 200 includes a piston carrier 205 that is located substantially within the piston carriage 100. As may be observed in more detail in FIGS. 14A-14C, at least the internal shape of the piston carrier 205 may substantially conform to the external shape of the syringe piston head 630. The exemplary piston carrier 205 further includes a distally located actuation collar 285 having a piston head retention lip 210, and a plurality of radially spaced apart apertures 215 that permit access through the wall of the piston carrier to the arms 630a, 630b of the piston head 630 by piston head release elements 305 of an exemplary syringe ejection mechanism, as further described below.

A plurality of spaced apart piston head release element guides 220 extend transversely outward from the actuation collar 285 of the piston carrier 205. As may be observed (see also FIGS. 17A-17B and 21A-21E), the inwardly-directed face 220a of each piston head release element guide 220 has a ramped (cammed) shape that directs movement of a distal portion of a corresponding one of the piston head release elements 305 during a syringe ejection operation. The outwardly-directed surface 220b of each piston head release element guide 220 may facilitate axial movement of the piston carrier 205 within the internal housing 35 and/or may function to rotationally restrain the piston carrier.

A proximal end 205a of the piston carrier 205 is configured to facilitate coupling of the piston carrier to a distal end of the armature shaft 265 of the dispensing solenoid assembly 250. Thus, in an assembled pipette 5, the piston carrier 205 is reciprocatable along with the piston carriage 100 by the motorized drive assembly 40, and is further independently reciprocatable within the piston carriage by the dispensing solenoid assembly 250.

Figure 15A:
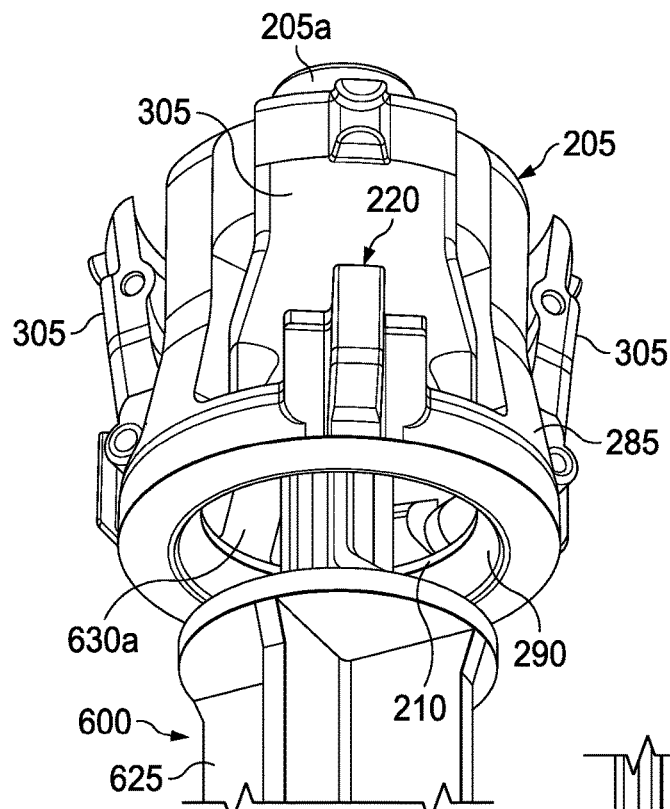
FIG. 15A is a deconstructed view showing the piston head of an exemplary syringe inserted into the piston carrier element of FIGS. 14A-14C, with certain piston release elements of an exemplary syringe ejection mechanism also present.
Figure 15B:
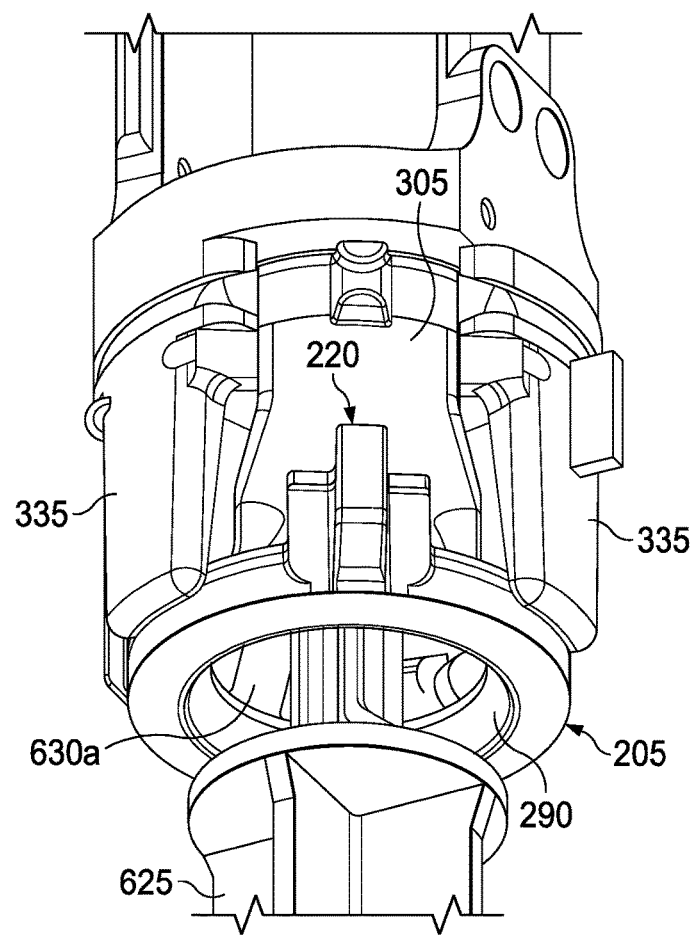
FIG. 15B is a slightly less deconstructed view of FIG. 15A, with additional elements of an exemplary syringe ejection mechanism also present.

A better understanding of the operation of the piston carrier 205 may be obtained by reference to the deconstructed views of FIGS. 15A-15B. FIG. 15A shows the exemplary syringe 600 with the piston head 630 thereof inserted into the piston carrier 205 of FIGS. 13 and 14A-14C, with the piston head release elements 305 of the exemplary syringe ejection mechanism pivotably located in the apertures 215 in the piston carrier. The piston head 630 preferably fits snugly within the interior of the piston carrier and, as may be observed, distal ends of the piston head arms 630a, 630b are engaged with the piston head retention lip 210 in the piston carrier 205, thereby preventing withdrawal of the piston head 630 from the piston carrier. Consequently, the piston head 630 is securely grasped by the piston carrier 205 and it is ensured that the piston 625 of the syringe 600 will move axially along with any axial movement of the piston carrier.

Figure 16:
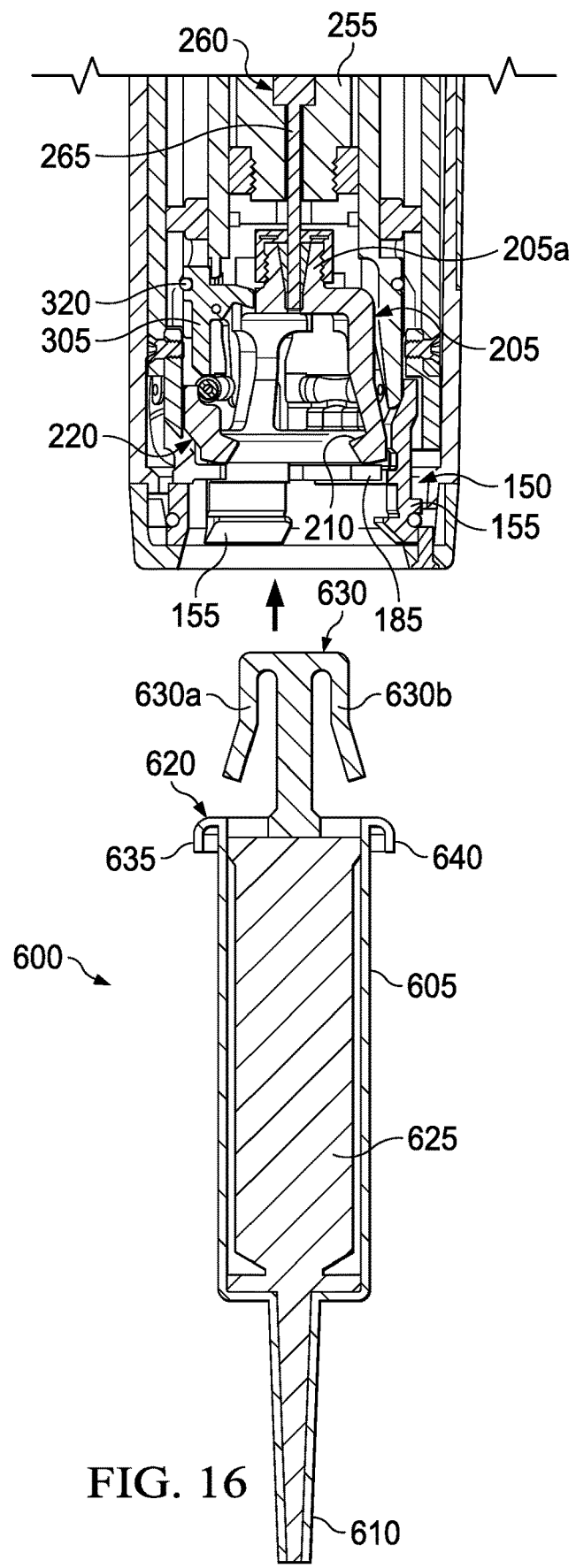
FIG. 16 indicates how an exemplary syringe is inserted into an exemplary motor-driven positive displacement pipette.
Figure 17A:
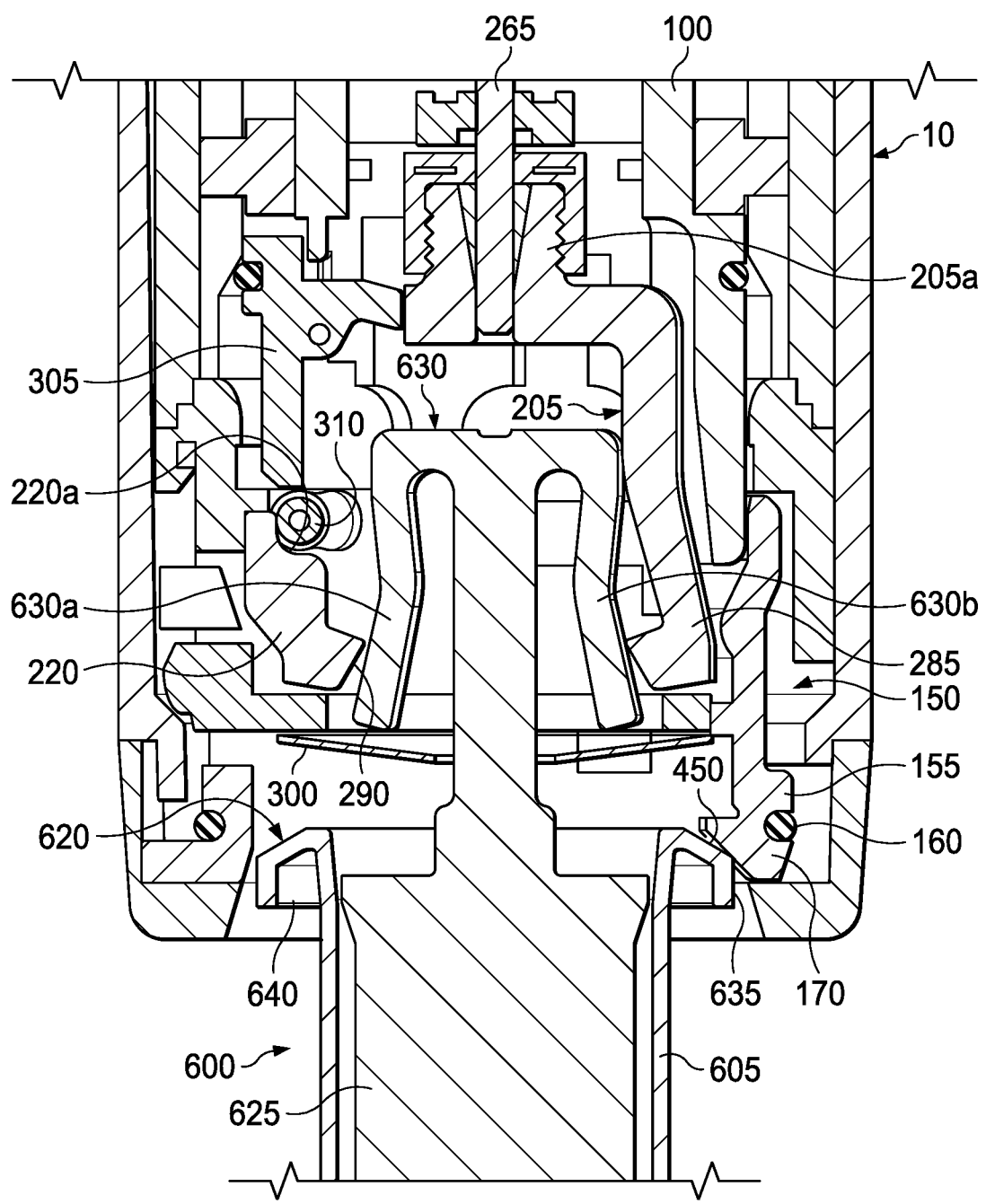
FIG. 17A is an enlarged view showing the syringe and pipette of FIG. 16 with the syringe partially inserted into the pipette such that the piston head of the syringe is only partly engaged by the piston head grasping mechanism of the pipette.
Figure 17B:
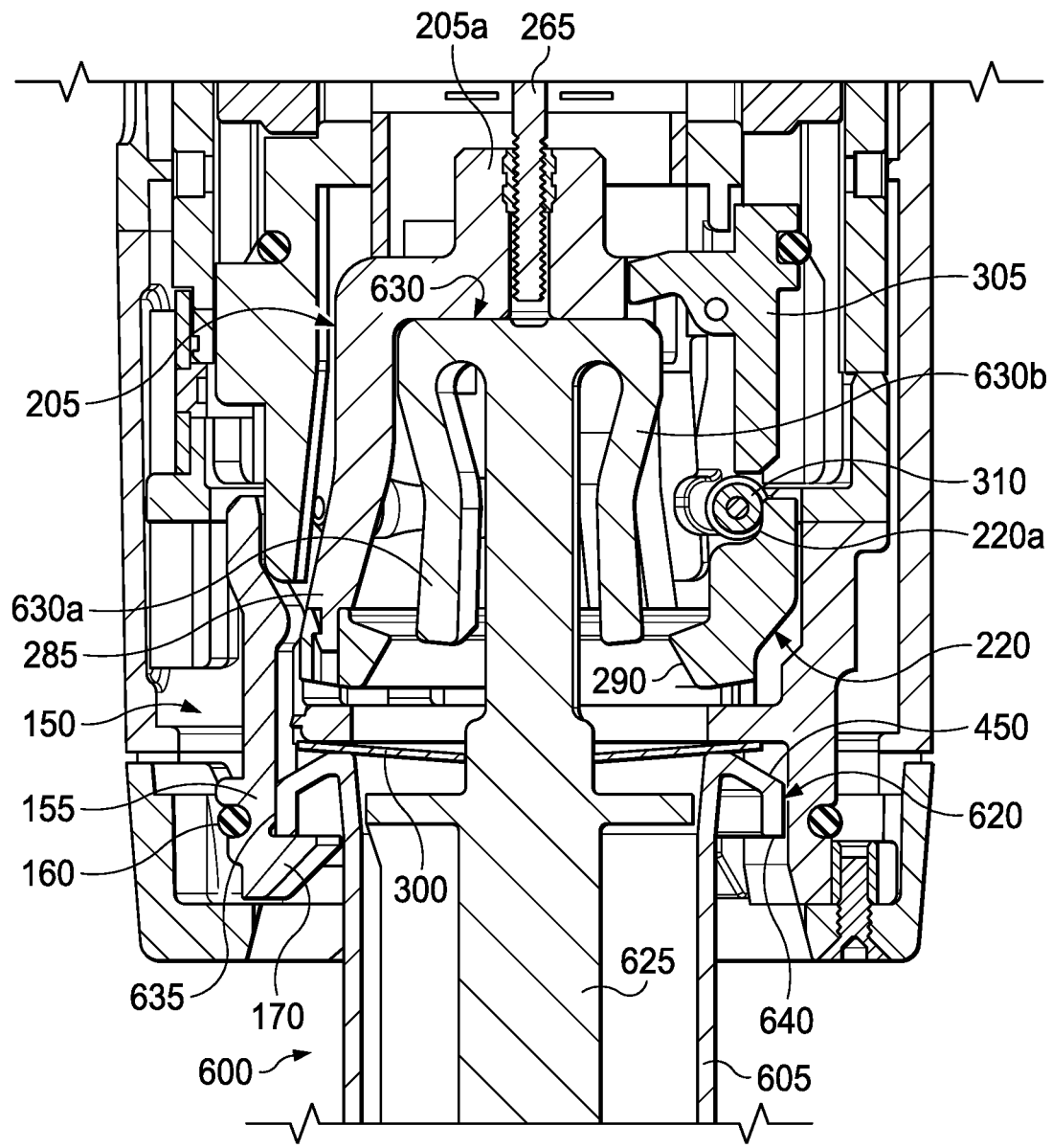
FIG. 17B is an enlarged view showing the syringe and pipette of FIG. 17A with the syringe inserted farther into the pipette but not yet fully engaged by the syringe retention mechanism thereof.

Referring now to FIGS. 16-17B, the process of inserting the exemplary syringe 600 to the exemplary pipette 5 may be observed. FIG. 16 shows the syringe 600 located below the distal end of the pipette 5 and in substantial axial alignment therewith. The arrow indicates the direction of engaging movement of the syringe 600 toward the pipette 5.

In FIG. 17A, the syringe 600 has been partially inserted into the pipette 5. During insertion of the syringe 600, the piston head 630 of the syringe piston 625 begins engagement with the piston carrier 205 of the syringe piston grasping mechanism 200. It may be observed in FIG. 17A that, during the syringe insertion process, the piston head arms 630a, 630b of the piston head 630 are inwardly compressed (i.e., undergo an inwardly-directed elastic deformation) via contact with a wall formed by the distal opening 290 in the actuation collar 285 of the piston carrier 205. The inward compression of the piston head arms 630a, 630b allows the syringe piston head 630 to pass through the distal opening in the actuation collar 285.

FIG. 17B depicts partial engagement of the syringe 600 and the pipette 5 resulting from continued insertion of the proximal end of the syringe 600 into the distal end of the pipette 5 beyond the point shown in FIG. 17A. Such continued insertion of the syringe 600 results in an outward pivotal movement of the distal ends of the syringe latching elements 155 under the insertion force applied to the syringe 600. More specifically, as the syringe 600 is inserted into the pipette 5, a resulting outwardly-directed force is exerted on the distal ends of the syringe latching elements 155 by the syringe retention element 620, which force is sufficient to overcome the inwardly-directed force exerted on the syringe latching elements by the O-ring 160.

As insertion of the syringe 600 into the pipette 5 continues, a proximal (upper) face of the syringe retention element 620 of the syringe capillary 605 comes into abutting contact with one or more springs 300 that are retained within the pipette 5. As may be observed in FIG. 17B, at the point of contact between the proximal (upper) face of the syringe retention element 620 and the spring(s) 300, the syringe retention element 620 has preferably moved past the latching hooks 170 of the syringe latching elements 155 (although a slight compression of the spring(s) may alternatively be required to reach said point), which permits the syringe latching elements 155 to be returned to their normally-closed positions by the contractive force of the O-ring 160. Upon return of the syringe latching elements 155 to their normally closed positions (see also FIGS. 18-19), a flat 175 on each syringe latching element hook 170 overlies and engages the lower face 640 of the syringe retention element 620 while an inward-facing surface 180 of each syringe latching element 155 is preferably pressed against the circumferential edge 635 of the syringe retention element by the contractive spring force of the O-ring 160. The syringe capillary 605 is thereby trapped against and releasably locked to the pipette 5, meaning that the syringe capillary is also securely retained in a stationary position relative to the pipette.

Subsequent to the releasable locking of the syringe 600 to the pipette 5, as shown in FIG. 17B and described above, the continued application of an insertion force on the syringe results in a slight but additional proximally-directed movement of the syringe into the pipette. This additional movement of the syringe 600 results from compression of the spring(s) 300 in the pipette by the insertion force being exerted on the syringe.

Figure 18:
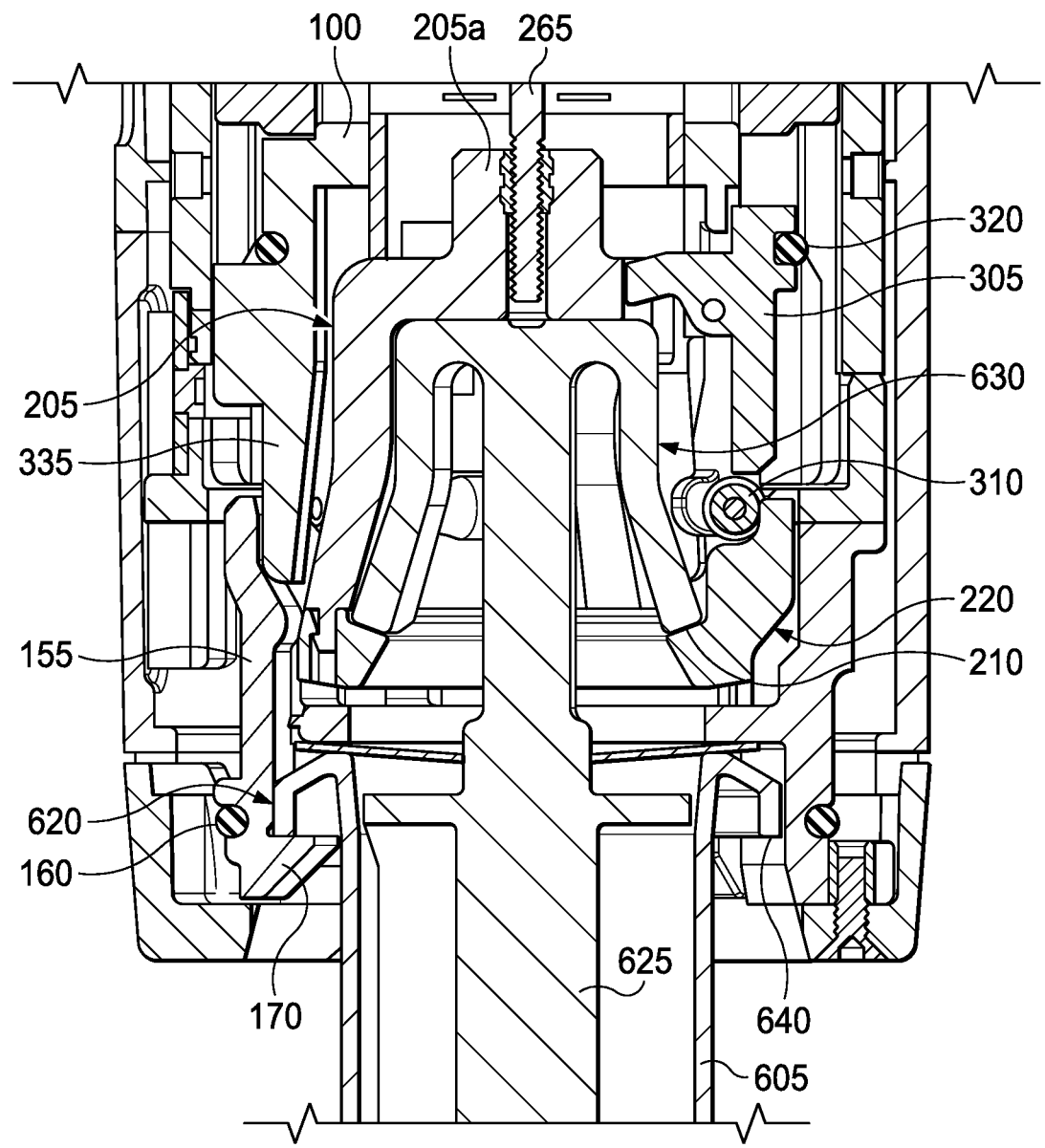
FIG. 18 shows the syringe and pipette of FIG. 17 with the syringe fully inserted into the pipette, such that the syringe is engaged by the syringe retention mechanism of the pipette and a piston head of the syringe is engaged by the syringe piston grasping mechanism of the pipette.

As illustrated in FIG. 18, the additional proximal movement of the syringe 600 into the pipette 5 allows the piston head 630 of the syringe to become fully inserted into the piston carrier, whereafter the piston head arms 630a, 630b will elastically return toward their normal static positions and become engaged with the piston head retention lip 210 located in the actuation collar 285 of the piston carrier, as shown in FIG. 18. The engagement of the piston head arms 630, 630b with the actuation collar 285 retains the piston head 630 in the piston carrier 205. It may also be observed in FIG. 18 that the piston head 630 fits snugly within the interior of the piston carrier 205 in this exemplary embodiment of the pipette 205.

Figure 19:
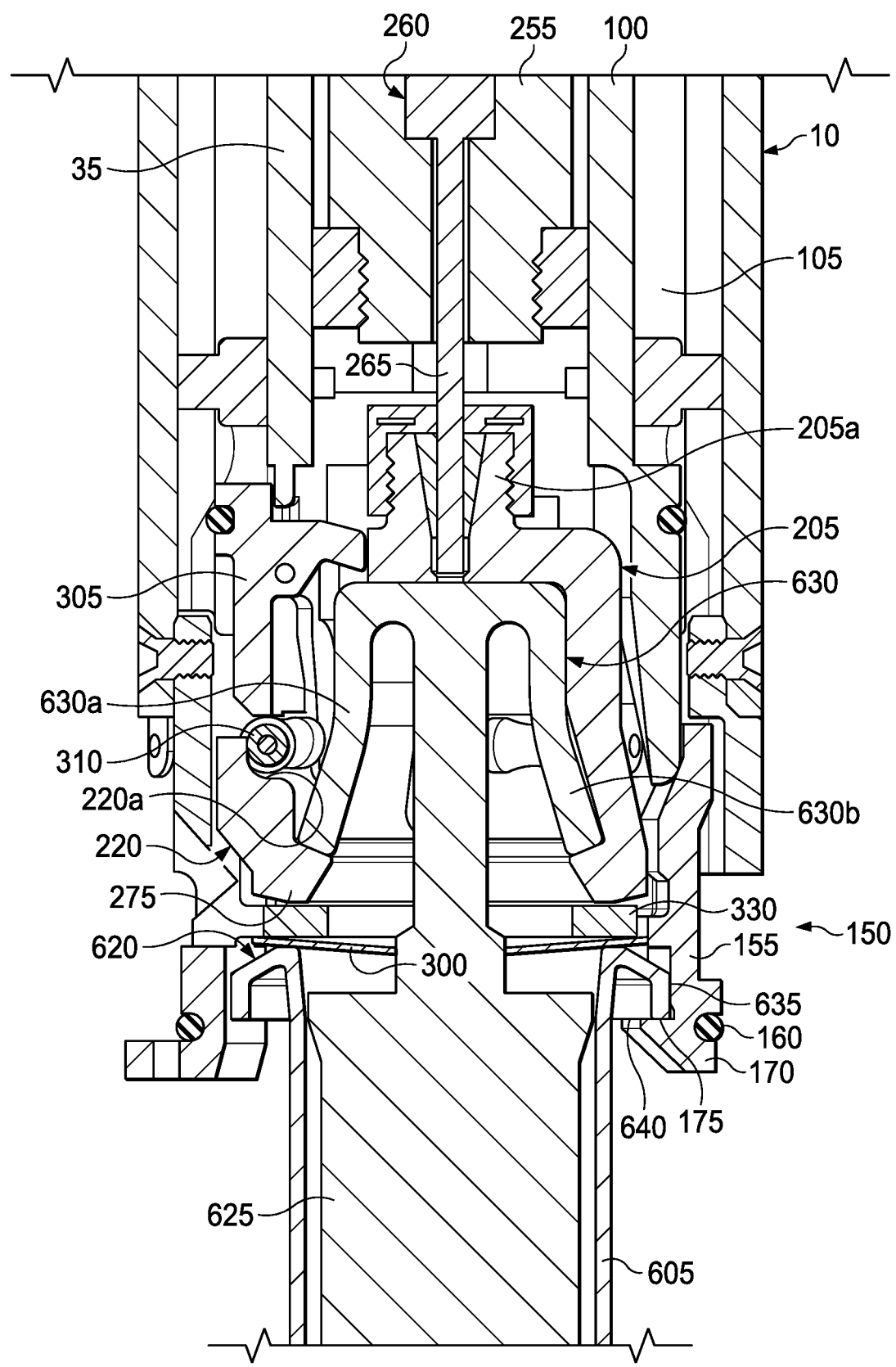
FIG. 19 is an enlarged, cross-sectional view of a portion of FIG. 18 showing the interaction of various components of the syringe retention mechanism and the syringe piston grasping mechanism with elements of the syringe.

In FIGS. 18-19, the syringe 600 is fully installed to the pipette 5. In the fully installed position, the syringe 600 is releasably locked to the pipette 5 as described above, and the piston head of the syringe is fully engaged by the syringe piston grasping mechanism 200 of the pipette. The syringe 600 is usable to aspirate and dispense fluids once placed in the fully installed position shown.

In addition to providing for additional insertion of the syringe 600 into the pipette 5 after the syringe retention element 620 of the syringe capillary 605 has reached an engaged position with the syringe retention mechanism 150 of the pipette, the spring(s) 300 also provides for increased retention security and stationary engagement of the syringe 600 to the pipette 5. More specifically, with the syringe 600 installed to the pipette 5, the spring(s) 300 exerts a distally-directed force against the upper face of the syringe retention element 620, which presses the lower face 640 of the syringe retention element tightly against the flats 175 of the hooks 170 of the syringe latching elements 155. The distally-directed force exerted by the spring(s) 300 also urges the piston head 630 toward the distal end of the pipette 5, which presses the distal ends of the piston head arms 630a, 630b tightly against the piston head retention lip 210 in the actuation collar 285 portion of the piston carrier 205. Therefore, any possible unintended movement of the syringe retention element 620 relative to the syringe latching elements 155 of the syringe retention mechanism 150 and/or movement of the piston head 630 relative to the piston carrier 205 is discouraged by the axially-directed force exerted by the spring(s) 300, thereby further securing the syringe 600 to the pipette 5. The spring(s) 300 may be, for example and without limitation, a sheet metal spring(s). The use of other types of springs may also be possible.

Because a positive displacement pipette syringe is disposable—i.e., intended to be discarded subsequent to completion of an associated pipetting operation—the exemplary syringe 600 must be ejectable from the pipette 5. As may be best understood from a review of the deconstructed perspective views of FIGS. 20A-20D and the cross-sectional views of FIGS. 21A-21F (see also FIGS. 13, 15A-15B, and 17A-19) the pipette 5 is provided with an exemplary syringe ejection mechanism for this purpose. Generally speaking, the syringe ejection mechanism is operative to decouple the syringe retention element 620 of the syringe 600 from the syringe retention mechanism 150 and to decouple the syringe piston head 630 from the piston carrier 205, whereafter the syringe will be automatically ejected from the pipette 5. As is explained in more detail below, the syringe ejection mechanism of the exemplary pipette 5 is comprised generally of the motorized drive assembly 40 and the lead screw 95, the piston carriage 100 and the wedge-shaped syringe latching element release portions 335 thereof, the syringe latching elements 155, the piston head release element guides 220 on the actuation collar portion 285 of the piston carrier 205, and a plurality of piston head release elements 305.

Figure 20A:
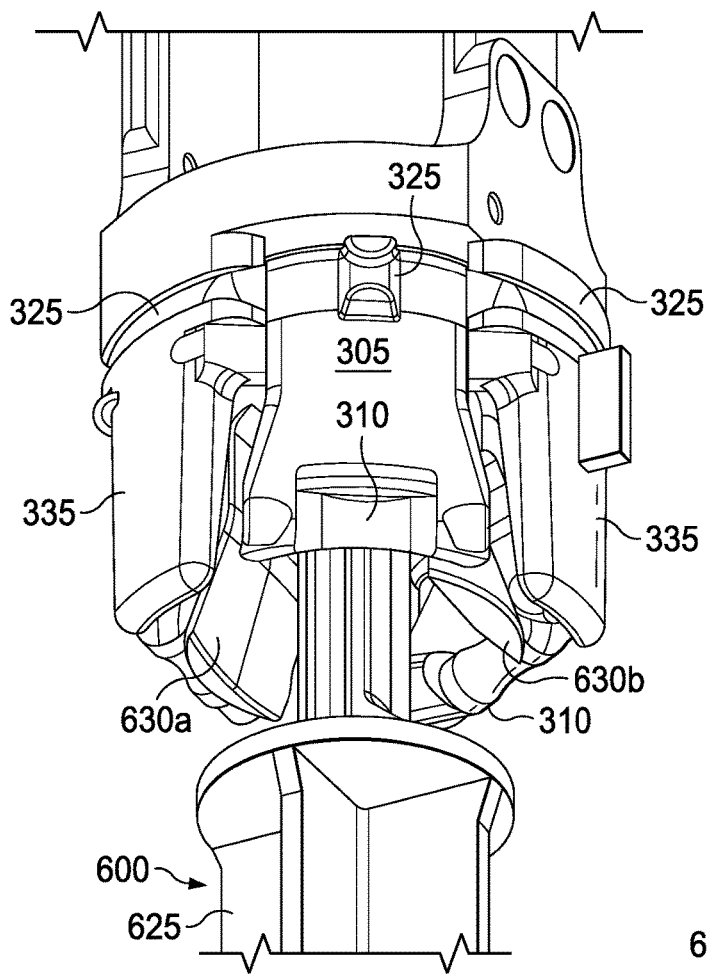
FIGS. 20A-20D illustrate various components of an exemplary syringe ejection mechanism of an exemplary motor-driven positive displacement pipette.
Figure 20B:
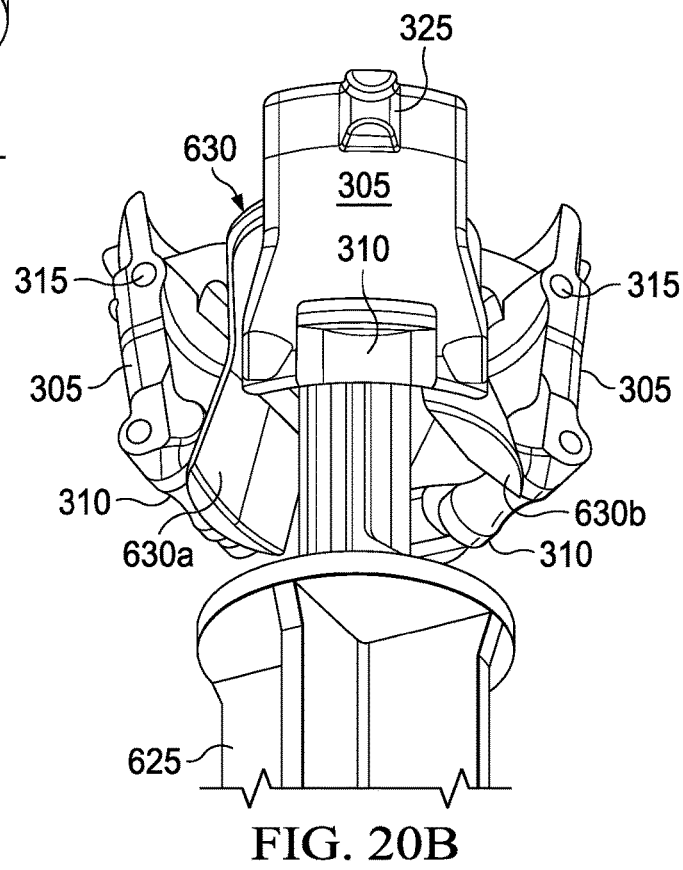
Figure 20C:
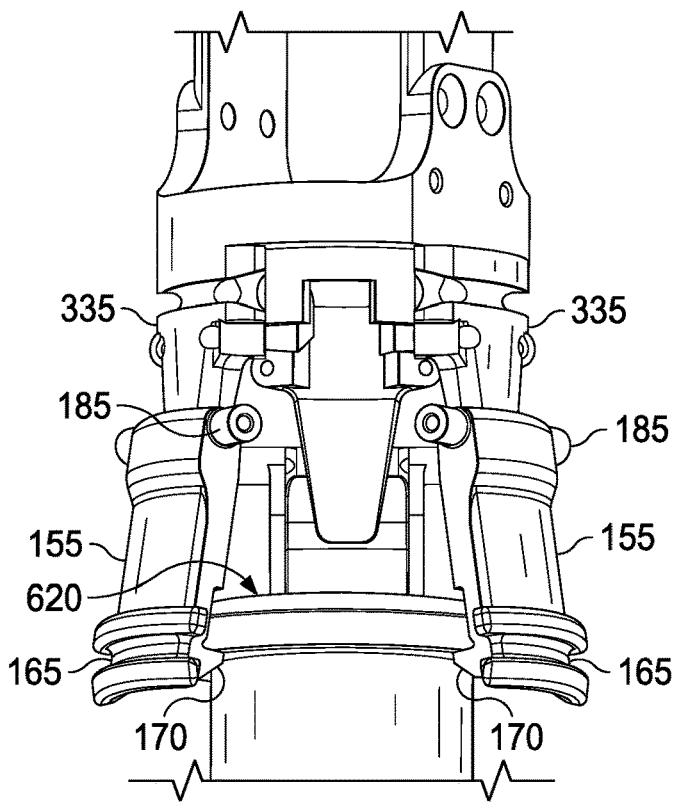

FIG. 20A essentially provides the same view of the piston head 630 of the exemplary syringe 600 inserted into the piston carrier 205 that is shown in FIG. 15A, except that in FIG. 20A the piston carrier 205 has been removed for further clarity. It may be observed in FIG. 20A that the piston head release elements 305 (which are shown to be aligned with the apertures 215 in the piston carrier 205 in FIG. 15A) of the syringe ejection mechanism are arranged to at least partially overlie the opposing arms 630a, 630b of the syringe piston head 630 when the piston head is inserted into the piston carrier 205. Each of the exemplary piston head release elements 305 may include a roller 310 at its distal end. The rollers 310 function to reduce friction between the piston head release elements 305 and the inwardly-directed ramped face 220a of each piston head release element guide 220 of the piston carrier 205, as well as between the piston head release elements and the arms 630a, 630b of the syringe piston head 630. However, it may be possible to eliminate the rollers 310 in other syringe ejection mechanism embodiments such as through the use of low friction materials, etc.

The piston head release elements 305 are pivotably secured within the piston carriage 100 by pins 315, such that an inwardly-directed movement of a proximal end of the piston head release elements will result in an outwardly-directed movement of a distal end of the piston head release elements. While not shown in FIGS. 20A-20D for purposes of clarity, the piston head release elements 305 are maintained in a normally open position (see, e.g., FIGS. 13, 16-19, 21A-21B, 22, and 24) by an O-ring 320 or another similar elastic element that encircles the piston head release elements 305 and resides within a slot 325 provided in each piston head release element. The O-ring 320 applies an inwardly-directed force against a proximal end of each piston head release element 305 so that the normally open position of the piston head release elements is a position where the distal ends of the piston head release elements are urged away from the piston carrier 205.

An exemplary syringe ejection operation is illustrated in FIGS. 21A-21F. During a syringe ejection operation, the piston carrier 205 is placed against a hard stop 225 and the motorized drive assembly 40 is commanded to cause a distally-directed movement of the piston carriage 100 of some predefined distance. In this exemplary embodiment of the pipette 5, the piston carriage is moved approximately 3.25 mm in the distal direction during a syringe ejection operation, but this distance may be different in other embodiments.

Because the piston carrier 205 is constrained against further distally-directed axial movement when against the hard stop 225, the aforementioned distally-directed axial displacement of the piston carriage 100 will cause a distally-directed axial displacement of the syringe latching element release portions 335 thereof relative to the piston carrier, as well as the piston head release elements 305 that are pivotably coupled to the piston carriage 100.

Figure 21A:
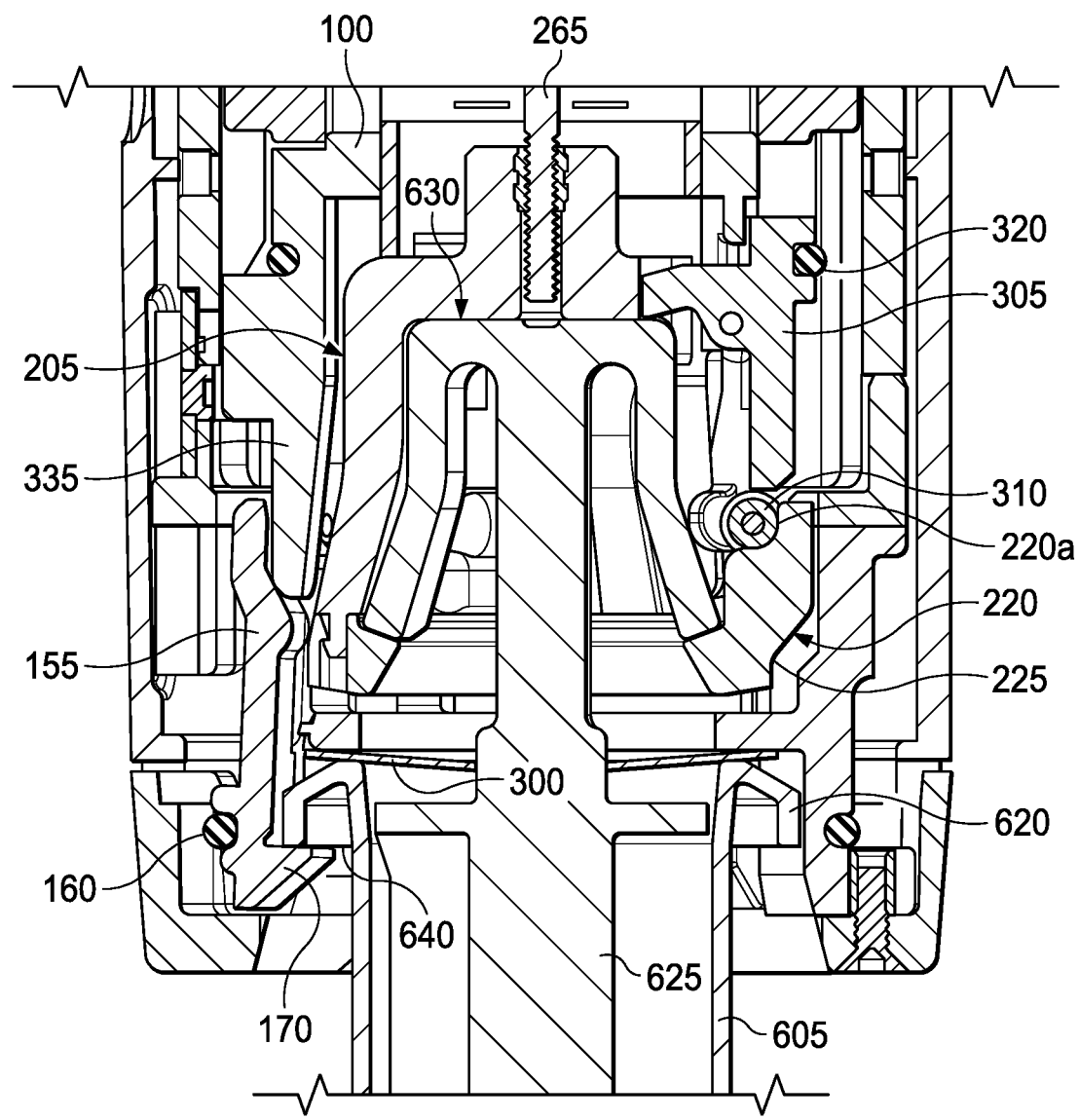
FIG. 21A illustrates the position of the various syringe ejection mechanism components of FIGS. 20A-20D along with other associated components of the pipette shortly after initiation of a syringe ejection operation.

Referring to FIG. 21A, it may be observed that as the piston carriage 100 moves distally, the syringe latching element release portions 335 of the piston carriage, which are arranged to be aligned with the syringe latching elements 155 and are positioned to move in a space between the syringe latching elements and the piston carrier 205, begin to contact the proximal ends of the syringe latching elements. Likewise, distal movement of the piston carriage 100 produces contact between the rollers 310 of the piston head release elements 305 and the inwardly-directed ramped face 220a of each piston head release element guide 220 associated with the actuation collar 285 of the piston carrier 205.

Figure 20D:
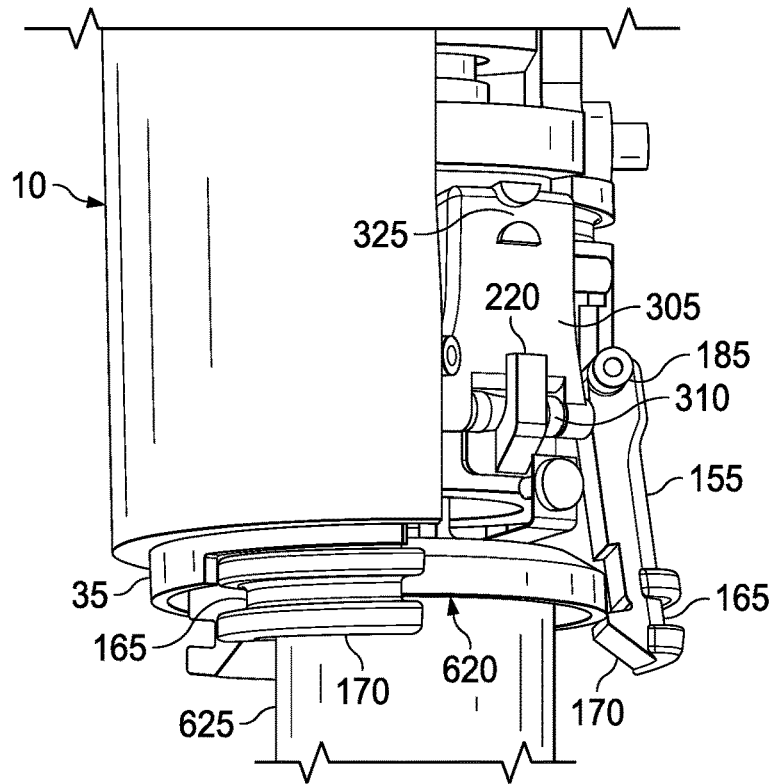
Figure 21B:
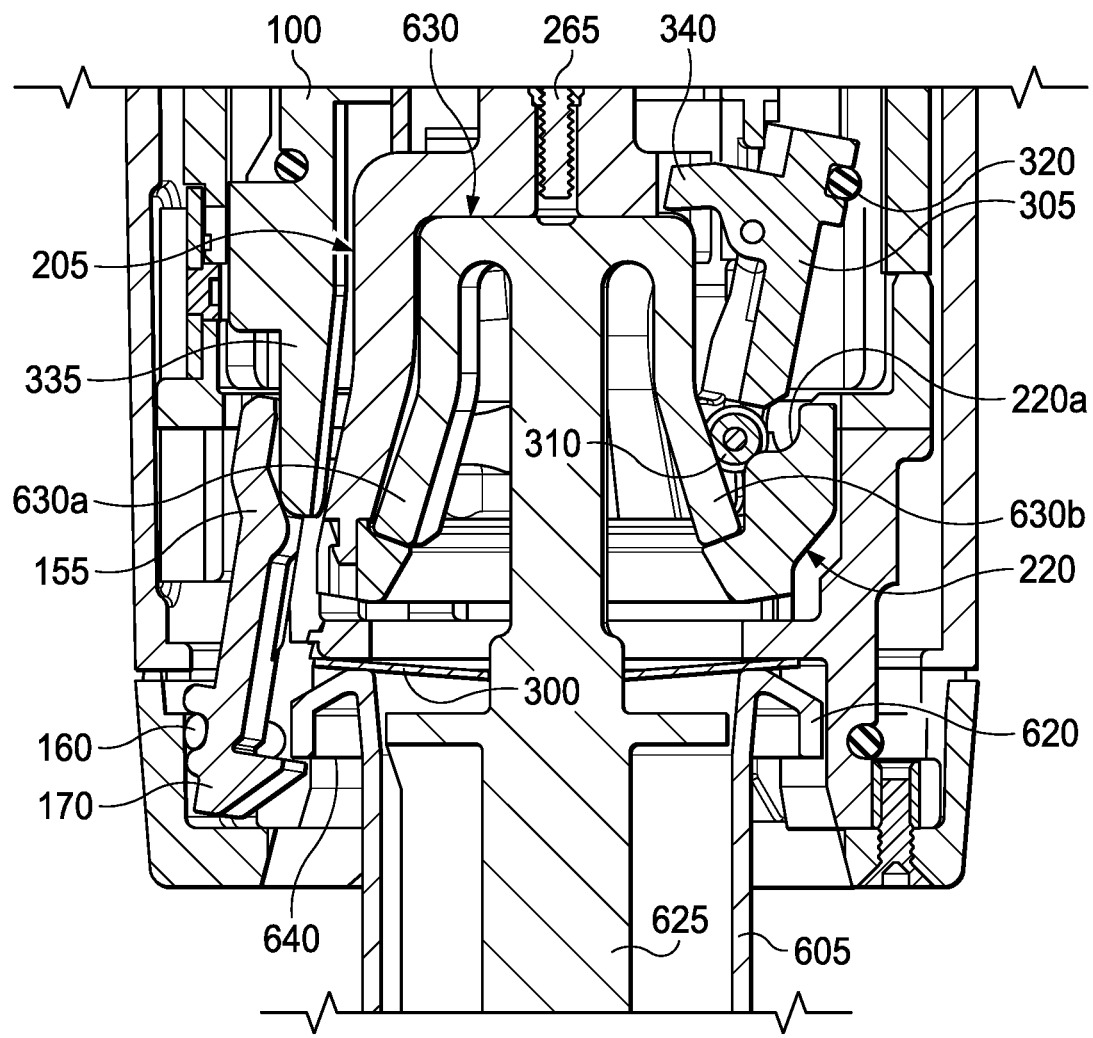
FIGS. 21B-21E further illustrate the position of the various syringe ejection mechanism components of FIGS. 20A-20D as a syringe ejection operation progresses.

FIG. 21B illustrates that a continued distal movement of the piston carriage 100 eventually results in sufficient contact between the wedge-shaped syringe latching element release portions 335 thereof and the proximal ends of the syringe latching elements 155, to cause the distal ends of the syringe latching elements to pivot outward about the mounting pins 185 and against the countering contractive force of the O-ring 160 and the axially-directed force of the spring(s) 300. As indicated, this pivoting movement of the syringe latching elements 155 causes the latching hooks 170 thereof to disengage from the syringe retention element 620 of the syringe 600 (as also shown in FIG. 20D), thereby releasing the syringe retention element and the syringe capillary 605 from retentive engagement with the pipette 5.

Figure 21C:
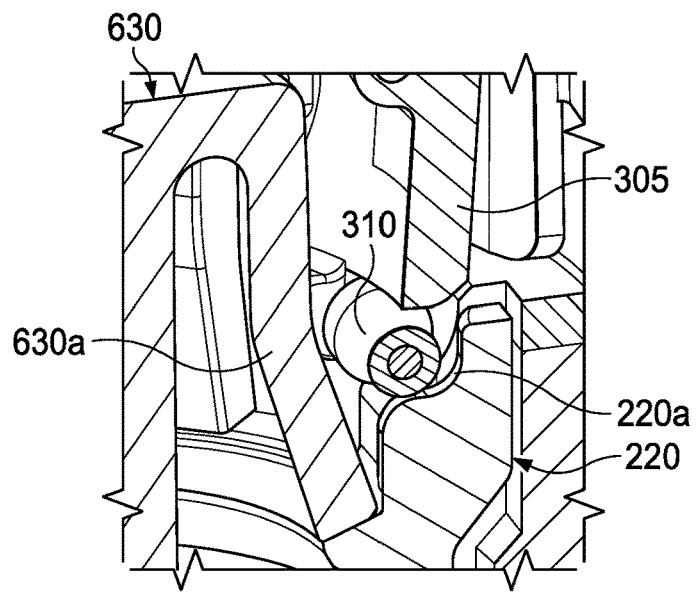
Figure 21D:
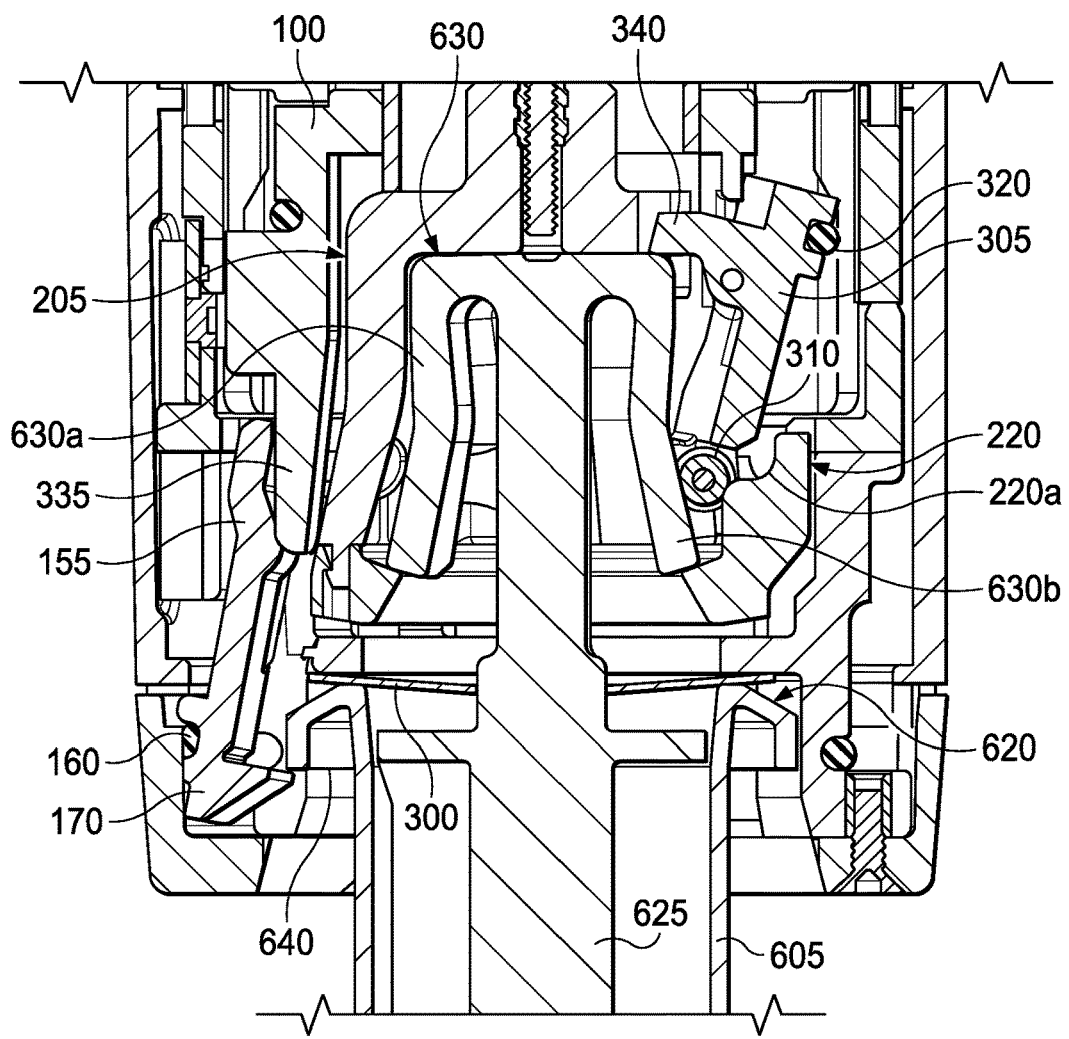
Figure 21E:
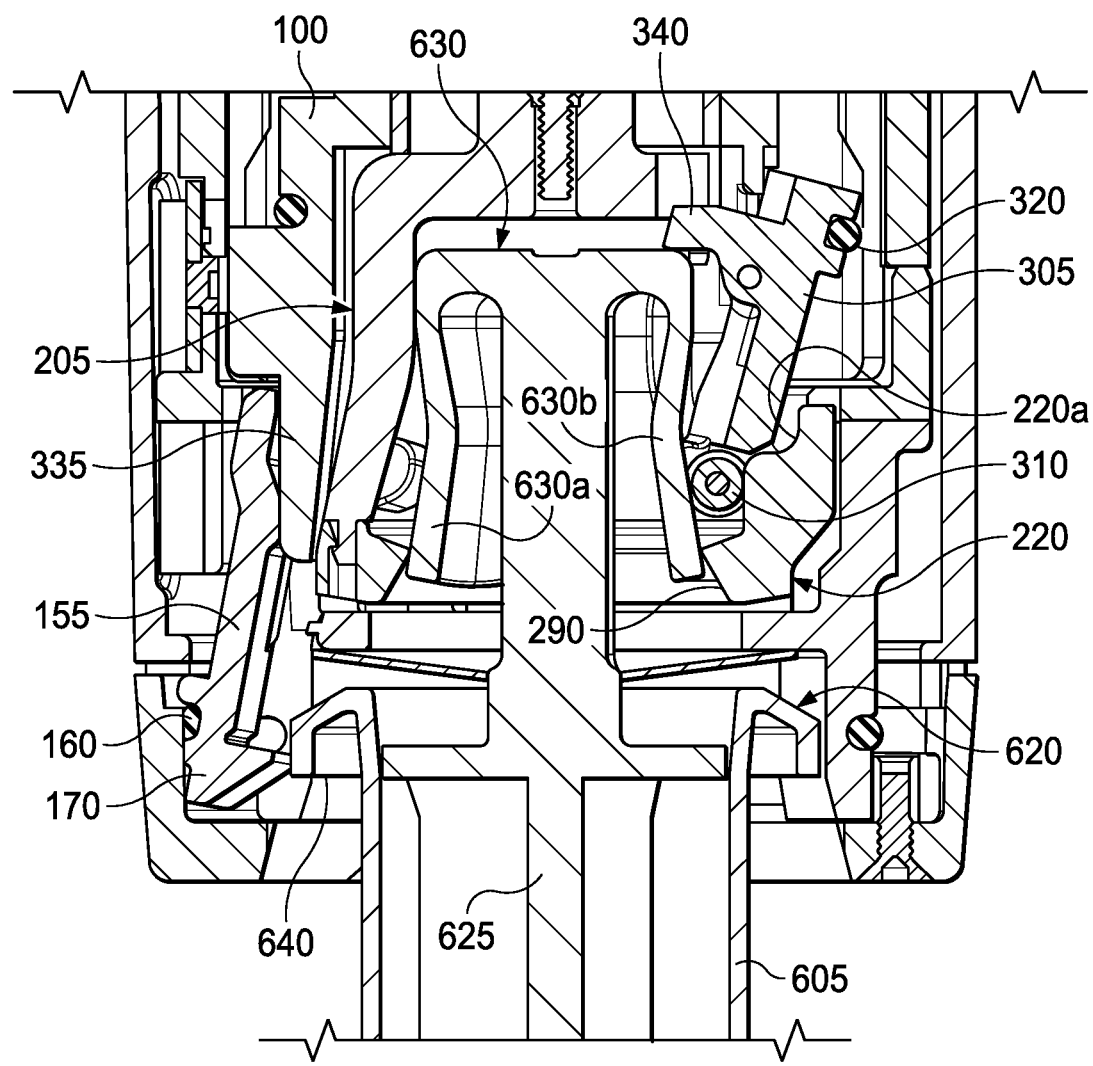
Figure 21F:
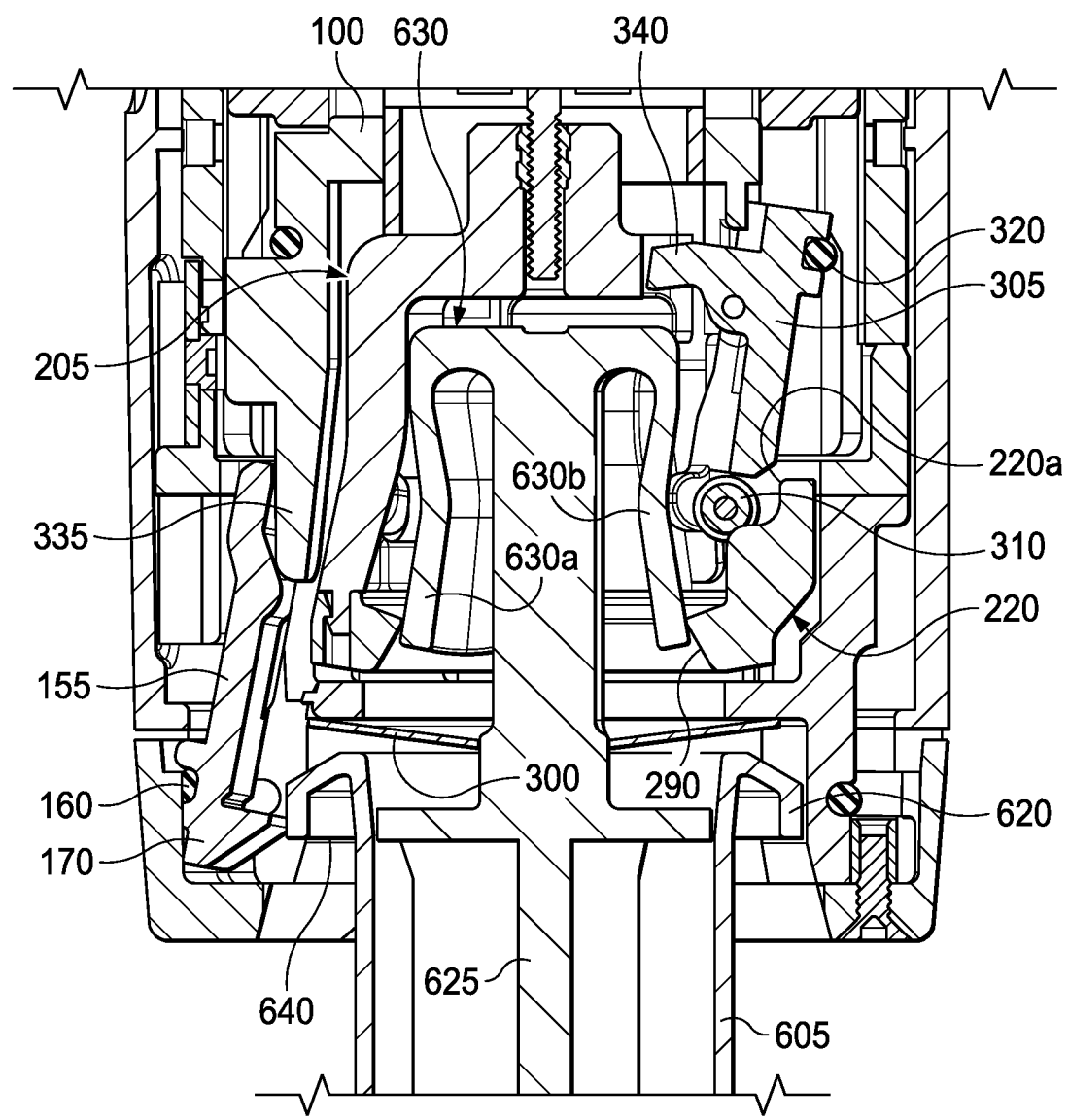
FIG. 21F represents the retractive movement of a piston carrier portion of the pipette during a last phase of an exemplary syringe ejection operation.

Referring now to FIGS. 21C-21E, it may be further observed that additional distal movement of the piston carriage 100 causes the rollers 310 of the piston head release elements 305 to follow the ramped face 220a of the correspondingly aligned piston head release element guides 220 of the piston carrier actuation collar 285. As a result, the distal ends of the piston head release elements 305 are pivoted inward toward the piston carrier 205. As shown in FIGS. 21D-21E, this inward movement of the distal ends of the piston head release elements 305 causes the rollers 310 attached thereto to enter the piston carrier 205 through the apertures 215 therein and to contact and begin to inwardly compress (deform) the opposing arms 630a, 630b of the syringe piston head 630.

As depicted in FIG. 21E, the amount of inward deformation of the syringe piston head arms 630a, 630b produced by the piston head release elements 305 is eventually sufficient to disengage the arms from the piston head retention lip 210 in the actuation collar 285 of the piston carrier 205. This disengagement of the syringe piston head arms 630a, 630b releases the piston head 630 from the piston carrier 205 and allows the syringe piston head 630 to be thereafter withdrawn in a proximal-to-distal direction through the distal opening 290 in the piston carrier.

As the piston head arms 630a, 630b are being inwardly compressed by the distal ends of the piston head release elements 305 during downward movement of the piston carrier 100, a proximally-located ejection tab 340 of each piston head release element simultaneously exerts a distally-directed (ejecting force) on the top of the piston head 630. This distally-directed force results in a like displacement of the piston head 630 and the capillary 605, and also causes the free ends of the piston head arms 630a, 630b to enter the distal opening 290 in the piston carrier 205.

With the syringe elements positioned as described above, the entire syringe 600 may be ejected from the pipette 5. In this exemplary embodiment, actual ejection of the syringe 600 occurs by first retracting the piston carriage 100 (see FIG. 21F) back to its home position, which retractive movement permits the piston head arms 630a, 630b to clear the rollers 310 of the piston head release elements 305 during ejection. Physical ejection may thereafter occur automatically as a result of gravity in combination with the axially-directed force exerted on the syringe retention element 620 by the spring(s) 300, and/or the syringe 600 may be removed from the pipette 5 by a user. The ejection movement as well as the return movement of the piston carriage 100 may occur automatically according to ejection operation program commands from the pipette controller 90.

Figure 22:
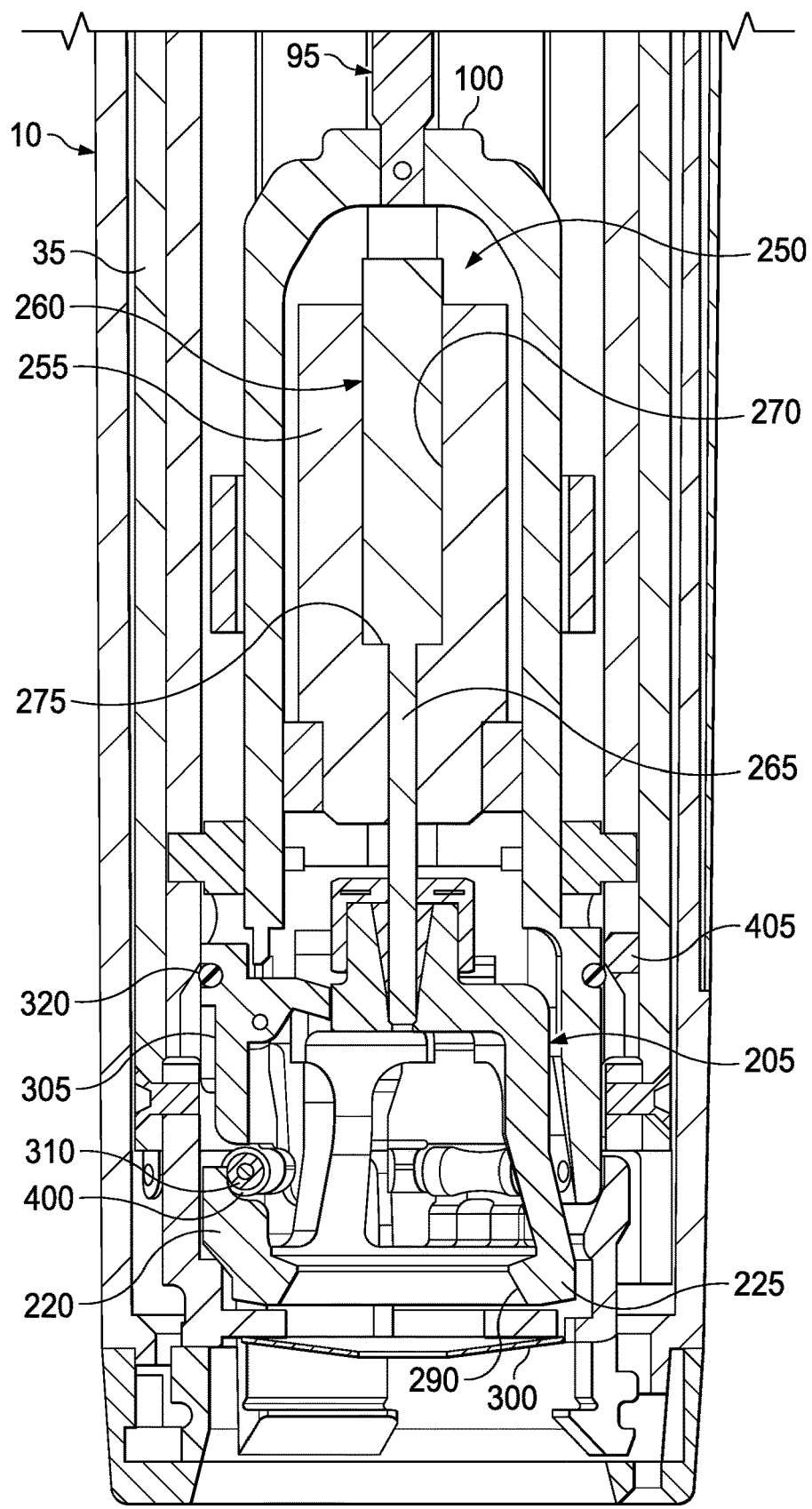
FIG. 22 is an enlarged cross-sectional side view of a portion of an exemplary motor-driven positive displacement pipette showing the various internal components thereof when the pipette is in a home position.

Various states and operations of the exemplary pipette 5 will now be described with respect to FIGS. 22-24. FIG. 22 represents a home position of the exemplary pipette 5. In the home position, the distal end of the piston carrier 205 essentially resides against the hard stop 225, with the understanding that residing "against" the hard stop allows for a minimal assembly clearance to exist between the hard stop and the piston carrier. Likewise, in the home position of the pipette 5, the armature 260 of the dispensing solenoid assembly 250 is at its distal hard stop against the bottom wall of the core 270 and the coil 260 of the dispensing solenoid assembly is not energized. In the home position of the pipette 5, the piston carriage 100 is distally positioned such that a slight gap 400 exists between the piston carrier 205 and the rollers 310 of the piston head release elements 305, such that there is no unintended interference between the rollers and the piston head 630 when the syringe is inserted into the pipette 5. A home position sensor 405 may be provided to indicate to the controller 90 that the piston carriage is in the home position.

Figure 23A:
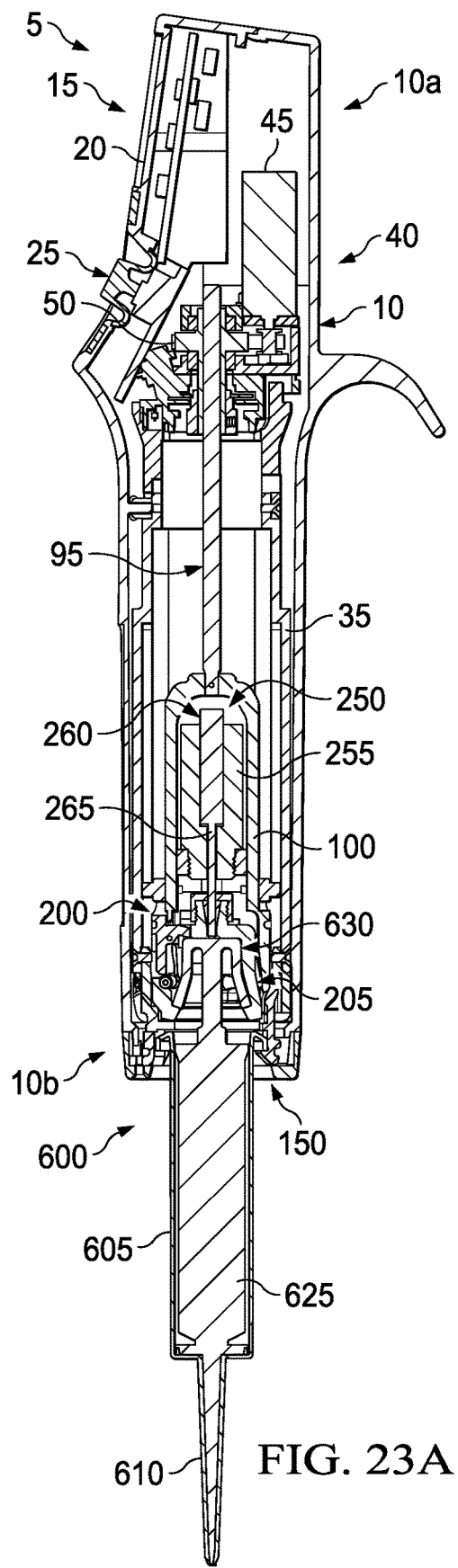
FIGS. 23A-23B are cross-sectional side views of an exemplary motor-driven positive displacement pipette with attached syringe according to the general inventive concept, and illustrate the change in position of various internal components of the pipette and the syringe piston when the pipette is moved from the home position to a ready to fully aspirated position, such as might result from a fluid aspiration operation.
Figure 23B:
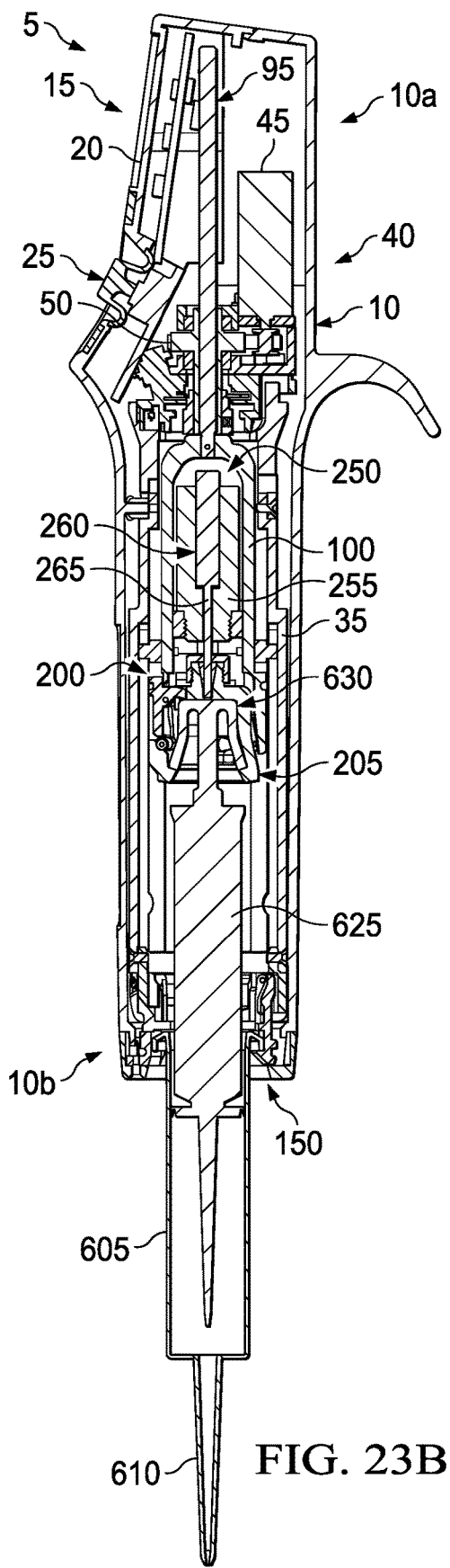
Figure 24:
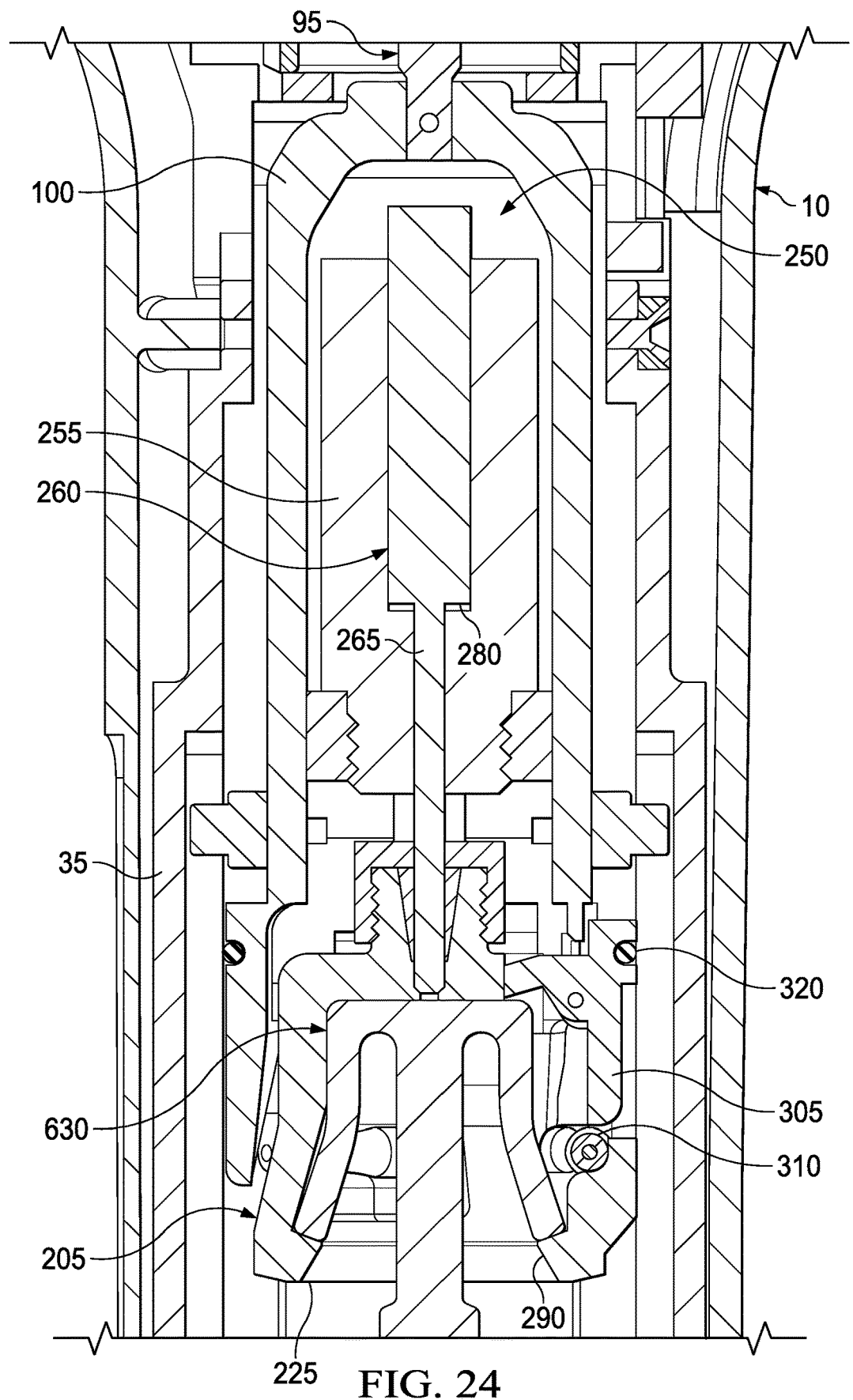
FIG. 24 depicts the change in position of various internal components of the exemplary pipette and syringe assembly from the fully aspirated position shown in FIG. 23B during one exemplary type of fluid dispensing operation.

An aspirating function of an exemplary pipette is represented in FIGS. 23A-23B through use of the exemplary pipette 5 and syringe 600 assembly of FIG. 2. FIG. 23A shows the exemplary pipette 5 in the home position, as described immediately above. It may be further observed that when the pipette 5 is in the home position with the syringe 600 installed thereto, the piston head 630 of the syringe piston 625 is engaged with the piston carrier 205 of the pipette but the piston has not yet been deliberately moved toward the proximal end of the pipette (beyond any incidental axial movement necessary to engage the piston head with the piston carrier). Consequently, the piston 625 still resides substantially against the distal interior of the syringe capillary 605.

The pipette assembly of FIG. 23B is depicted in a ready to dispense or fully aspirated position—i.e., the pipette 5 is shown to have performed an aspiration function by which a full syringe volume of a fluid of interest is drawn into the syringe 600. It is also possible to aspirate less than a full syringe volume of fluid. To aspirate the fluid, the tip 610 of the syringe 600 is placed in the fluid and an aspiration program is initiated via the user interface portion 15 of the pipette or a user manipulates an actuator to energize the motor 45 of the motorized drive assembly 40, to drive the piston carriage 100 and the associated components coupled thereto some desired distance toward the proximal end of the pipette 5. This proximally-directed axial movement of the piston carriage 100 produces a like movement of the solenoid body 260 which, in turn, produces a like movement of the armature 260 and the piston carrier 205 that is attached to the armature shaft 265. Since the head 630 of the syringe piston 625 is engaged with the piston carrier 205, the syringe piston is also moved proximally an equal distance within the syringe capillary 610, which draws the fluid of interest into the now evacuated capillary.

When the exemplary pipette 5 is in the fully aspirated position such as that shown in FIG. 23B, various ones of the pipette components will still reside in the same positions relative to other components as when the pipette resides in the home position. For example, the armature 260 of the dispensing solenoid assembly 250 remains at its distal hard stop 275 against the bottom wall of the bore 270 and the coil 260 of the dispensing solenoid assembly is not energized. Likewise, the gap 400 between the piston carrier 205 and the rollers 310 of the piston head release elements 305 is also maintained when the pipette 5 is in an aspirated position.

The action of the various pipette components during a dispensing operation are described with reference to FIGS. 23B and 24. The specific manner in which the dispensing components of the pipette 5 are activated during a dispensing operation is dependent on the selected dispensing volume. That is, small volume dispensing is preferably performed using the solenoid assembly 250 while large volume dispensing is preferably performed using the motorized drive assembly 40 alone or the motorized drive assembly 40 in combination with the solenoid assembly 250.

The delineation between a small dispensing volume and a large dispensing volume may vary across different pipette embodiments, because the largest volume of fluid that can be dispensed by the solenoid assembly 250 alone is dependent on the maximum stroke of the solenoid armature 260, which is in turn, determined by the maximum distance the piston carriage 100 may be moved from the fully aspirated position toward the distal end of the pipette 5 before causing an unintended dispensing of fluid from the syringe 600. For purposes of illustration, and not limitation, the maximum piston carriage displacement that may be produced without causing unintended dispensing is 0.5 mm in this exemplary embodiment of the pipette 5.

Because the solenoid body 255 is coupled to the piston carriage 100, the solenoid body moves toward the distal end of the pipette 5 during like movements of the piston carriage. However, since the armature 260 of the solenoid floats freely within the bore in the solenoid body 255, because the solenoid armature is also coupled to the piston carrier 205 by the armature shaft 265, and because the piston carrier is biased toward the proximal end of the pipette 5 by the pressure of the aspirated fluid in the syringe 600 pushing against the syringe piston 670, the solenoid armature remains in its current position and does not move with the piston carriage and the solenoid body during the aforementioned movement of the piston carriage. This creates a solenoid stroke gap 280 between the distal face 260b of the armature 260 and the bottom wall of the bore 270 in the solenoid body 255 of a distance that is commensurate with the aforementioned distal movement of the piston carriage 100 (up to 0.5 mm in this example). This solenoid stroke gap 280 is the maximum stroke of the solenoid armature 260 and thus, in this exemplary embodiment of the pipette 5, is also 0.5 mm.

A 0.5 mm maximum stroke of the solenoid armature 260 results in a corresponding dispensing volume of approximately 0.01 (1%) of the total volume of the given syringe installed to the pipette. Consequently, for this particular example, a small dispensing volume would be considered to be about 0.001 ml or less of the 0.1 ml volume syringe 500, about 0.01 ml or less of the 1.0 ml volume syringe 550, about 0.1 ml or less of the 10 ml volume syringe 600, about 0.25 ml or less of the 25 ml volume syringe 650, and about 0.5 ml or less of the 50 ml volume syringe 700. Dispensing volumes greater than these approximate small volume dispensing volumes would be considered large volume dispensing volumes in this particular example. Note that the smallest deliverable dispensing volume using the motorized drive assembly 40 alone or the motorized drive assembly 40 in combination with the solenoid assembly 250, is generally the same as the largest deliverable dispensing volume using the solenoid assembly alone (although there may be some overlap).

Upon initiation of a small volume dispensing operation, the controller 90 of the pipette 5 instructs the motorized drive assembly 40 to move the piston carriage 100 some distance (less than or equal to 0.5 mm, depending on the selected small volume to be dispensed) toward the distal end of the pipette. The specific distance by which the piston carriage 100 moves is dependent on the selected small volume of fluid to be dispensed. The maximum piston carriage 100 displacement distance and resulting solenoid armature 260 stroke in this exemplary pipette 5 is 0.5 mm.

With the piston carriage 100 moved to the small volume dispensing position and the gap 280 in the solenoid assembly resultingly created, the controller 90 temporarily energizes the solenoid body 255 which, as would be understood by one of skill in the art, creates a magnetic field that rapidly and forcefully fires the armature 260 toward the distal end of the pipette 5 and into halting contact with the armature hard stop 275. This rapid and distally directed movement of the solenoid assembly armature 260 produces a like movement of the piston carrier 205 and the syringe piston 625 that is coupled therewith, which causes the selected dispensing volume of fluid to jet out from the tip 610 of the syringe 600 with sufficient velocity to break any surface tension between the fluid and the inner wall surface of the syringe capillary 610 and to thereby ensure that the last drop of fluid is dispensed without the need to touch off the syringe tip 610 on the receiving vessel. The process of moving the piston carriage 100 and dispensing a small fluid volume by firing the solenoid assembly 250 may be repeated until the aspirated volume is fully dispensed or until a desired number of dispensing operations have been completed.

As may be understood from the foregoing description, large volume dispensing in the context of the exemplary pipette, is simply the dispensing of fluid volumes greater than the maximum possible fluid volumes that are dispensable by action of the solenoid assembly alone. Therefore, with respect to the exemplary pipette 5 and the exemplary syringes 500, 550, 600, 650, 700 shown and described herein, large volume dispensing encompasses dispensing volumes greater than about 0.001 ml of the 0.1 ml volume syringe 500, greater than about 0.01 ml of the 1.0 ml volume syringe 550, greater than about 0.1 ml of the 10 ml volume syringe 600, greater than about 0.25 ml of the 25 ml volume syringe 650, and greater than about 0.5 ml of the 50 ml volume syringe 700. The maximum volume that can be dispensed during a single large volume dispensing operation is the entire volume of the given syringe 500, 550, 600, 650, 700.

As mentioned above, two methods of large volume dispensing may be possible. According to a first method, large volume dispensing is performed using the motorized drive assembly 40 alone, while according to a second method, large volume dispensing is performed using the motorized drive assembly 40 in combination with the solenoid assembly 250. The employed large volume dispensing method may be dependent on the specific construction of the pipette and possibly also on the properties of the fluid to be dispensed.

In accordance with the first method of large volume dispensing method mentioned above, it has been found that when dispensing a large fluid volume, or at least when dispensing a fluid volume that falls within some volume range of the overall large volume dispensing range of the exemplary pipette 5, dispensing may be performed without the need for assistance from the solenoid assembly 250. More specifically, it has been found that when dispensing large fluid volumes, movement of the piston carriage 100 alone, coupled with an increase in fluid velocity resulting from the fluid in the syringe 600 being forced from the larger diameter capillary 605 through the much smaller diameter tip 610 and orifice 615, may be sufficient to produce a fluid dispensing velocity that is great enough to overcome any surface tension between the fluid and the inner wall surface of the syringe capillary and to thereby ensure that the last drop of fluid is dispensed from the syringe without the need to touch off the syringe tip on the receiving vessel.

Large volume dispensing by movement of the piston carriage 100 alone may be automatically directed by the pipette controller 90 based on the dispensing program selected by a user, the syringe installed to the pipette 5, the dispensing volume associated with the selected dispensing program, etc. In any event, upon initiation of a large volume dispensing operation by means of piston carriage 100 movement only, the controller 90 determines the displacement of the piston carriage required to eject the selected large volume of fluid to be dispensed. The motorized drive assembly 40 subsequently rotates the drive nut 50 to linearly displace the lead screw 95 and the piston carriage 100 until the gap 400 between the piston carrier 205 and the rollers 310 of the piston head release elements 305 is closed, which produces a like displacement of the piston carrier 205 and the syringe piston 625 that is engaged therewith. Dispensing of the selected large fluid volume is thus accomplished.

Alternatively, large volume dispensing may be accomplished by a combination of piston carriage movement and firing of the solenoid assembly 250. As with the first large volume dispensing method, the second large volume dispensing method may be automatically selected by the pipette controller 90 based on the dispensing program selected by a user, the syringe installed to the pipette 5, the dispensing volume associated with the selected dispensing program, etc. In any event, upon initiation of the second large volume dispensing operation the controller 90 again determines the displacement of the piston carriage required to eject the selected large volume of fluid to be dispensed. The motorized drive assembly 40 subsequently rotates the drive nut 50 to linearly displace the lead screw 95 and the piston carriage 100 by the required distance, which produces a like displacement of the piston carrier 205 and the syringe piston 625 that is engaged therewith, and a corresponding dispensing of fluid from the syringe Upon completion of piston carriage 100 movement and the corresponding dispensing of fluid from the syringe 600, the controller 90 temporarily energizes the solenoid body 255, which fires the armature 260 of the solenoid assembly 250 toward the distal end of the pipette 5 and into halting contact with the armature hard stop 275. This rapid and distally directed movement of the solenoid assembly armature 260 produces a like movement of the piston carrier 205 and the syringe piston 625, which will dispense any non-dispensed fluid remaining in the syringe tip 610 due to surface tension between the fluid and the inner wall surface of the syringe capillary 610. Thus, it can be ensured that the last drop of the fluid volume intended to be dispensed is actually dispensed and not inadvertently retained in the syringe tip 610. When the volume of fluid dispensed during a large volume fluid dispensing operation is less than the total volume of fluid in the syringe 600, the dispensing operation may be repeated until a desired number of dispensing operations have been completed, until the fluid volume is exhausted, or until the remaining fluid volume is insufficient to perform another dispensing operation of a desired fluid volume.

Dispensing operations using the exemplary pipette 5 may be accomplished via a selected pipetting program that operates the pipette in an automatic (auto) mode or via a manual mode. As briefly mentioned above, a user is able to access and selectively initiate a desired pipetting program through the user interface portion 15 of the pipette 5.

Auto mode dispensing may encompass a number of different and selectable dispensing procedures. One simplistic example of such a dispensing procedure results in aspiration of a full syringe volume of fluid, followed by dispensing of the entirety of the aspirated fluid volume in one dispensing operation.

In another auto mode dispensing procedure example, a volume of fluid is aspirated into the syringe 600 as previously described, and is subsequently dispensed in multiple doses of equal volume until a desired number of dispensing operations have been completed, until the fluid volume is exhausted, or until the remaining fluid volume is insufficient to perform another dispensing operation of selected fluid volume. In yet another auto mode dispensing procedure example, a volume of fluid is aspirated into the syringe 600 as previously described, and is subsequently dispensed in multiple doses of variable volume until a desired number of dispensing operations have been completed, until the fluid volume is exhausted, or until the remaining fluid volume is insufficient to perform another dispensing operation of a desired fluid volume. In still another auto mode dispensing procedure example, a volume of fluid is aspirated into the syringe 600 as previously described, and is subsequently dispensed in multiple doses of equal or variable volume until some portion (e.g., 50%) of the aspirated volume has been dispensed. At this point, another aspiration operation is performed to increase the volume of fluid in the syringe 600 and dispensing is performed again. This process may be repeated until a desired number of dispensing operations have been completed, until the fluid volume is exhausted, or until the remaining fluid volume is insufficient to perform another dispensing operation of selected fluid volume.

In any of the above-described exemplary auto mode dispensing procedures, the aspirated volume of fluid may be the entire fluid volume of the installed syringe, or some lesser volume. Dispensing of the fluid may be accomplished by firing of the solenoid assembly 250 alone, by movement of the piston carriage 100 alone, or by a combination thereof. As described above, the dispensing method used may be selected based on the pipette construction (e.g., resolution), the installed syringe, the desired dispensing volume, some combination thereof, and/or on other factors.

The menu of exemplary procedures that may be performed under the auto mode of an exemplary pipette may further include a titration procedure. As would be understood by one of skill in the art, a titration procedure using the exemplary pipette 5 generally involves adding some amount of a titrant that has been aspirated in to the syringe 600 to a container of analyte and indicator until the indicator changes color or achieves some other observable characteristic, indicating that the reaction has reached a state of neutralization. Since the amount of titrant that will need to be added to the analyte solution to reach neutralization is typically unknown, the titration program may include a titrated volume counter that indicates the volume of titrant that has been dispensed. The counter may be resettable to allow for multiple titration operations from a single aspirated volume of titrant.

A dispensing operation may also be performed by a user in a manual mode rather than by the controller 90 of the pipette 5 operating in auto mode. In manual mode, the user operates the motorized drive assembly 40 to produce a fast or slow aspiration and/or dispensing of fluid from the syringe 600.

An exemplary pipette may also be provided with fluid viscosity detection capability. More specifically, the viscosity of a fluid of interest may be determined indirectly such as by providing the pipette with appropriate circuitry 350 (see FIG. 5B) or other means for monitoring and analyzing the increased current draw by the drive motor resulting from the increased motor torque required to move the syringe piston relative to the syringe capillary during an aspiration or dispensing operation; through use of a provided load cell 355 (see FIG. 5B) that measures the force required to move the syringe piston relative to the syringe capillary during an aspiration or dispensing operation; by way of a mechanical spring; or via another technique that would be understood by one of skill in the art.

When utilizing a current draw monitoring technique, the value of the current draw may be used to categorize the viscosity of the fluid, and the pipette controller may adjust the dispensing operation parameters of the pipette based on the identified fluid viscosity category. For example, and without limitation, if the fluid of interest is determined to have a low viscosity, the controller may apply normal dispensing settings during a fluid dispensing operation. If the fluid of interest is determined to have a medium viscosity, the controller may increase the voltage to the drive motor and may also enforce a suck back mode (a retraction of the lead screw that draws air into the syringe capillary) for aliquots that would normally not require suck back during dispensing of fluids of low viscosity. If the fluid of interest is determined to have a high viscosity, the controller may disable the solenoid assembly so dispensing is possible only via movement of the piston carriage, and may also notify a user that syringe tip touch-off will be required to ensure no liquid is left in the syringe tip.

An exemplary pipette, such as the exemplary pipette 5, may also be programmed to performed a discard dispense function. The discard dispense function is preferably a part of pipetting process when using the exemplary pipette 5, and may be enforced by the controller 90. Generally speaking, the discard dispense function is operative to remove any backlash and to account for any manufacturing and/or assembly tolerance issues in the drive, solenoid, and overall system, and may also remove any air that is entrapped near the distal end of the syringe tip. The controller 90 may be programmed to initiate a discard dispense function after each aspiration operation. The discard dispense function may also be initiated any time all of the fluid previously aspirated into a syringe is fully dispensed. The discard dispense volume will be variable based on the viscosity of the liquid being worked with and the syringe construction.

Another possible exemplary pipette feature that may be provided according to the general inventive concept is automatic syringe identification functionality. Because an exemplary pipette is usable with syringes of many different volumes, it is realized that it would be beneficial if an exemplary pipette could automatically identify the syringe volume when the syringe is installed to the pipette. Such an ability would allow the controller of the pipette to automatically select the appropriate operating parameters for the given syringe volume, thereby simplifying the setup process and possibly eliminating operator error associated with mistakenly identifying the volume of a syringe being used.

In one exemplary embodiment, color coding is used as a mechanism for syringe identification. More specifically, each syringe volume is associated with a different color and an area of corresponding color is located on the syringe.

Using the exemplary syringes 500, 550, 600, 650, 700 depicted in FIGS. 6A-10B as examples, a color band 450, 455, 460, 465, 470 that corresponds to the volume of each given syringe is placed along an upper shoulder 520a, 570a, 620a, 680a, 730a of the syringe retention element 520, 570, 620, 680, 730. In some embodiments, the color band 450, 455, 460, 465, 470 of a given syringe may extend only partially around the syringe retention element as shown in FIGS. 6A, 7A, 8A, 9A and 10A, while in other embodiments a color band 450', 455', 460', 465', 470' may extend around the entire circumference of the syringe retention element, as shown in FIGS. 6C, 7C, 8C, 9C and 10C. Color coding may also be provided in the form of a continuous patch of color, a discrete patch of color, or in any other readable form such as without limitation, a collection of dots, segmented lines, etc. Color may also be molded into the material from which a given syringe retention element is made. It is also possible, as represented in FIGS. 6A, 7A, 8A, 9A and 10A, that color coding, such as a color band 750, 755, 760, 765, 770 or otherwise, may be located on the syringe piston instead of or in addition to, on the syringe retention element of a given syringe, for imaging by an appropriately located color sensor(s) within or on a given pipette.

Figure 25:
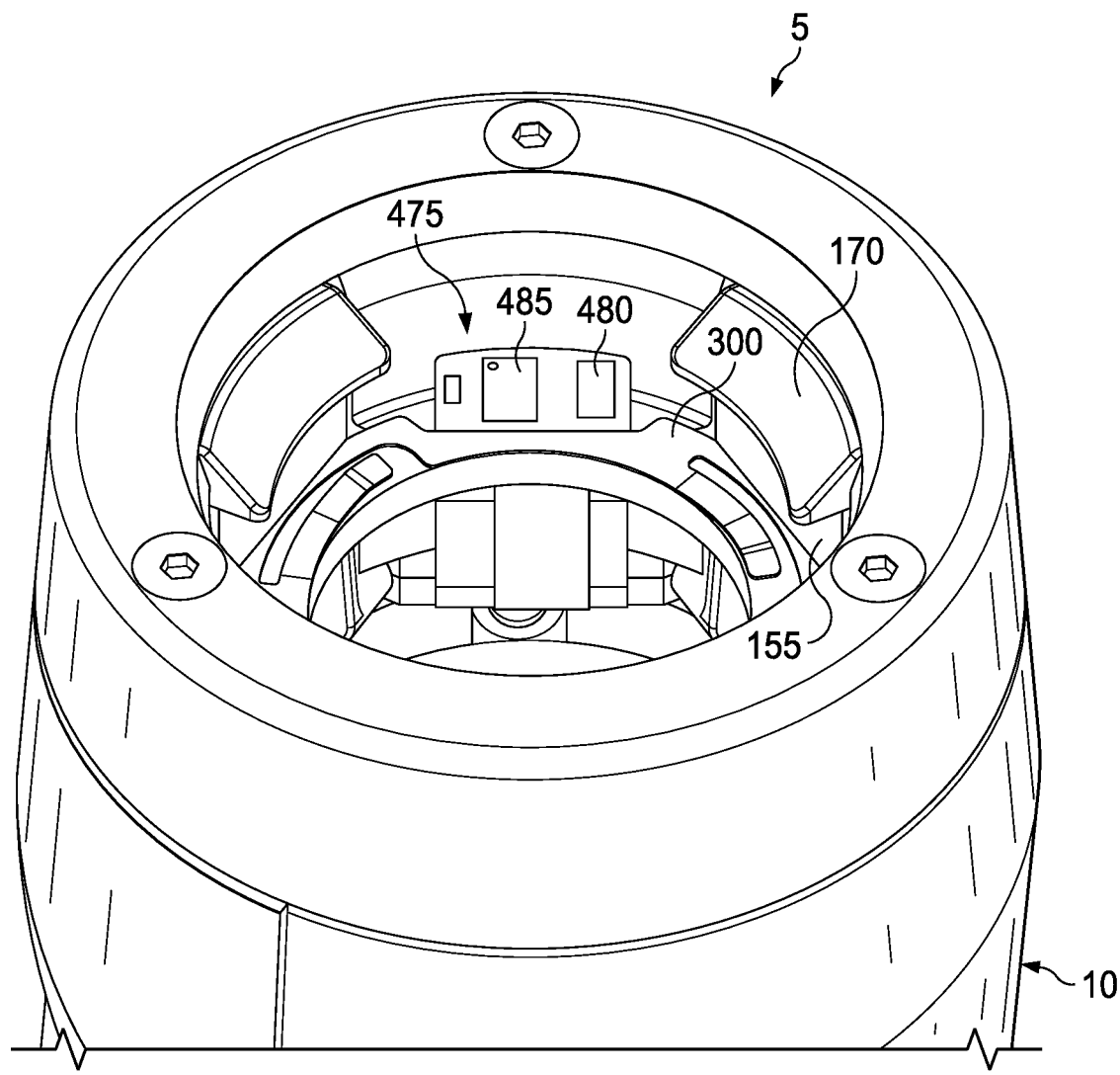
FIG. 25 is a bottom perspective view of an exemplary motor-driven positive displacement pipette where a color sensor is visible along with various other components.

As illustrated in FIG. 25, one or more color sensors 475 may reside within the distal end of the exemplary pipette 5, and may be configured and located to image the color bands 450, 455, 460, 465, 470 or 450', 455', 460', 465', 470' on the syringe retention elements 520, 570, 620, 680, 730 of the exemplary syringes 500, 550, 600, 650, 700. Upon installation of an exemplary syringe 500, 550, 600, 650, 700 to the pipette 5, the color sensor(s) 475 images the color band 450, 455, 460, 465, 470 and transmits a signal to the pipette controller 90 that is indicative of the color of the color band. The controller 90 is provided with the proper data (e.g., a lookup table, etc.)—such as for example through a process of preliminary and offline color recognition and registration operation using the color sensor(s) 475—to analyze the signals received from the color sensor(s) 475 to identify the color of the color band 450, 455, 460, 465, 470 and, thus, the volume of the installed syringe 500, 550, 600, 650, 700. As described above, with the syringe volume identified, the controller 90 may proceed to automatically set any of various pipetting parameters and/or to indicate the syringe volume to a user of the pipette 5.

In the exemplary pipette and syringe embodiments presented herein, the upper shoulders 520a, 570a, 620a, 680a, 730a of the syringe retention elements 520, 570, 620, 680, 730 are preferably chamfered at some angle (e.g., between 30° and 60° relative to the upper face of the retention element). The chamfered upper shoulders 520a, 570a, 620a, 680a, 730a of the syringe retention elements 520, 570, 620, 680, 730 facilitate insertion of the syringe retention elements into the pipette 5. Additionally, the chamfered upper shoulder 520a, 570a, 620a, 680a, 730a of each syringe retention elements provide an angled surface from which light emitted by the emitter portion (illumination source) 480 of the color sensor 475 can be reflected toward the detection face 485 of the color sensor 475, which may be mounted to the pipette at a corresponding angle. Use of such a chamfered shoulder further allows for a color band to be applied using a vertical pad printing process, which is the most efficient way of printing.

While color sensing using a color sensor 475 to read color coding on the chamfered upper shoulders 520a, 570a, 620a, 680a, 730a of the syringe retention elements 520, 570, 620, 680, 730 is shown and described herein for purposes of illustration, it is to be understood that exemplary pipette embodiments are not limited to this arrangement. For example, and without limitation, a sensor(s) may instead be located within an exemplary pipette so as to read color coding, printing, etc., on other areas of a syringe, such as the exemplary color bands 750, 755, 760, 765, 770 shown on the syringe piston heads in FIGS. 6A, 7A, 8A, 9A and 10A.

While certain embodiments of the general inventive concept are described in detail above for purposes of illustration, the scope of the general inventive concept is not considered limited by such disclosure, and modifications are possible without departing from the spirit of the general inventive concept as evidenced by the following claims:

What is claimed is:

1. A pipette system having syringe identification functionality, comprising:
    a handheld powered positive displacement pipette comprising:
        a color sensor located within and at a side of a distal end of the pipette, said color sensor operable to differentially recognize reflected visible light of at least a group of various colors and provide color identification data to the controller; and
        a syringe retention mechanism;
    a controller in communication with the color sensor and configured to receive data signals therefrom including the color identification data; and
    a syringe configured for use with, and installation at, the pipette to form a unitary device, said syringe comprising: a syringe retention element and a color coding provided at a surface of the syringe retention element having a given color of the group of various colors, said surface extending at an angle between 30 degrees and 60 degrees from a longitudinal axis of the syringe, said color coding provided at a location on the surface that resides within a field of view of the color sensor when the syringe is installed to the pipette, the given color of the color coding indicating at least one distinct characteristic of the syringe from other syringes of a group of syringes, each having the color coding with a different respective color of the group of various colors;
    wherein the controller is programmed to use the color identification data received from the color sensor to differentially identify the syringe installed to the pipette from the other syringes of the group of syringes and to automatically set or adjust one or more operating parameters of the pipette based on the differential identification;
    wherein the syringe retention mechanism temporarily secures the syringe from removal from the pipette by way of at least the syringe retention element when the pipette is sufficiently inserted axially at the distal end of the pipette.

2. The syringe identification system of claim 1, wherein the controller is a component of the pipette.

3. The syringe identification system of claim 1, wherein the surface of the syringe retention element is provided by a chamfered shoulder such that the color coding is located on the chamfered shoulder, said chamfered shoulder extending laterally beyond an outer perimeter of a capillary of the syringe.

4. The syringe identification system of claim 3, wherein the color sensor is coupled to the pipette body so as to be oriented substantially normal to the chamfered shoulder of the syringe retention element when the syringe is installed to the pipette such that the color sensor extends at an angle between 30 degrees and 60 degrees from a longitudinal axis of the syringe to match the angle of the surface from the longitudinal axis of the syringe.

5. The syringe identification system of claim 1, wherein each of the syringes of the group of syringes have different internal volumes.

6. The syringe identification system of claim 1, wherein the at least one characteristic of the syringe indicated by the given color of the color coding is or includes the syringe volume, and the controller is further programmed to identify the syringe volume when identifying the syringe installed to the pipette.

7. The syringe identification system of claim 1, wherein the color coding is selected from the group consisting of a colored marking, a continuous patch of color, a discrete patch of color, a collection of dots, and a collection of segmented lines.

8. The syringe identification system of claim 1, wherein the controller is provided with a lookup table of syringe identification data associated with each of a plurality of different color coding colors comprising the group of various colors.

9. The syringe identification system of claim 1, wherein the color coding is molded into the syringe.

10. The syringe identification system of claim 1, wherein the color sensor includes an illumination source.

11. The syringe identification system of claim 1, wherein the color coding extends completely around the syringe retention element.

\* \* \* \* \*

UNITED STATES PATENT AND TRADEMARK OFFICE
CERTIFICATE OF CORRECTION

PATENT NO. : 11,911,767 B2
APPLICATION NO. : 16/664769
DATED : February 27, 2024
INVENTOR(S) : Hill et al.

Page 1 of 1

It is certified that error appears in the above-identified patent and that said Letters Patent is hereby corrected as shown below:

On the Title Page

Page 2, Column 2 In Item (56), References Cited, Foreign Patent Documents, Line 17 please delete "IN 108136119 A 6/2018" and insert -- CN 108136119 A 6/2018 --.

Signed and Sealed this
Twenty-third Day of April, 2024

Katherine Kelly Vidal
*Director of the United States Patent and Trademark Office*